United States Patent
Wilson

(10) Patent No.: US 9,216,015 B2
(45) Date of Patent: Dec. 22, 2015

(54) APPARATUS AND METHODS FOR PERFORMING BRAIN SURGERY

(75) Inventor: Jeffrey A. Wilson, Wrenthem, MA (US)

(73) Assignee: Vycor Medical, Inc., Boca Raton, FL (US)

( * ) Notice: Subject to any disclaimer, the term of this patent is extended or adjusted under 35 U.S.C. 154(b) by 2060 days.

(21) Appl. No.: 11/665,667

(22) PCT Filed: Oct. 28, 2005

(86) PCT No.: PCT/US2005/038828
§ 371 (c)(1),
(2), (4) Date: Apr. 18, 2007

(87) PCT Pub. No.: WO2006/050047
PCT Pub. Date: May 11, 2006

(65) Prior Publication Data
US 2009/0048622 A1 Feb. 19, 2009

Related U.S. Application Data

(60) Provisional application No. 60/622,991, filed on Oct. 28, 2004.

(51) Int. Cl.
*A61B 19/00* (2006.01)
*A61B 17/02* (2006.01)
(Continued)

(52) U.S. Cl.
CPC ......... *A61B 17/0218* (2013.01); *A61B 17/3431* (2013.01); *A61B 17/3439* (2013.01);
(Continued)

(58) Field of Classification Search
CPC ........... A61B 17/0218; A61B 17/3431; A61B 17/3439; A61B 19/201; A61B 19/5212
USPC ......... 600/101, 103, 114, 184; 606/108, 130, 606/190–191, 194
See application file for complete search history.

(56) References Cited

U.S. PATENT DOCUMENTS 2,769,441 A 11/1956 Abramson
2,922,415 A 1/1960 Campagna
(Continued)

FOREIGN PATENT DOCUMENTS

JP 02289221 11/1990
JP 05344978 12/1993
(Continued)

OTHER PUBLICATIONS

Taisuke Otsuke et al; "Stereotactic Guiding tube for Open-System Endoscopy: A new Approach for the Stereotactic Endoscopic Resection of intra-Axial Brain Tumore"; Neurosurgery, vol. 27, No. 2; Aug. 1990; pp. 326-330.
(Continued)

*Primary Examiner* — Ashley Fishback
(74) *Attorney, Agent, or Firm* — RatnerPrestia

(57) ABSTRACT

Less invasive surgical techniques for performing brain surgery are disclosed in which a dilating obturator and cannula assembly is inserted into brain tissue until the obturator tip and cannula are adjacent to the target tissue. The obturator is removed and surgery is performed through the cannula. In preferred embodiments the obturator and cannula are placed using image guidance techniques and systems to coordinate placement with pre-operative surgical planning. A stylet with associated image guidance may be inserted prior to insertion of the obturator and cannula assembly to guide insertion of the obturator and cannula assembly. Surgery preferably is performed using an endoscope partially inserted into the cannula with an image of the target tissue projected onto a monitor. Dilating obturator structures having a rounded or semi-spherical tip and/or an optical window for visualizing brain tissue during expansion are contemplated.

10 Claims, 18 Drawing Sheets

(51) Int. Cl.
*A61B 17/34* (2006.01)
*A61B 17/00* (2006.01)

(52) U.S. Cl.
CPC ............ *A61B19/201* (2013.01); *A61B 19/5212* (2013.01); *A61B 19/5244* (2013.01); *A61B 2017/00907* (2013.01); *A61B 2017/3456* (2013.01); *A61B 2019/208* (2013.01)

(56) References Cited

U.S. PATENT DOCUMENTS

| | | |
|---|---|---|
| 3,417,746 A | 12/1968 | Moore |
| 3,608,547 A | 9/1971 | Sato |
| 3,626,471 A | 12/1971 | Florin |
| 3,690,323 A | 9/1972 | Wortman et al. |
| 3,766,910 A | 10/1973 | Lake |
| 3,882,855 A | 5/1975 | Schulte |
| 3,888,117 A | 6/1975 | Lewis |
| 4,263,900 A | 4/1981 | Nicholson |
| 4,312,353 A | 1/1982 | Shahbabian |
| 4,386,602 A | 6/1983 | Sheldon |
| 4,502,468 A | 3/1985 | Burgin |
| 4,636,199 A | 1/1987 | Victor |
| 4,638,798 A | 1/1987 | Shelden et al. |
| 4,931,039 A | 6/1990 | Coe |
| 4,945,896 A | 8/1990 | Gade |
| 5,052,373 A | 10/1991 | Michelson |
| 5,135,526 A | 8/1992 | Zinnanti |
| 5,160,323 A | 11/1992 | Andrew |
| 5,183,464 A | 2/1993 | Dubrul et al. |
| 5,230,623 A | 7/1993 | Guthrie |
| 5,249,568 A | 10/1993 | Brefka |
| 5,251,127 A | 10/1993 | Raab |
| 5,256,149 A * | 10/1993 | Banik et al. ............... 604/164.01 |
| 5,271,380 A | 12/1993 | Riek |
| 5,275,583 A | 1/1994 | Crainich |
| 5,305,203 A | 4/1994 | Raab |
| 5,320,611 A | 6/1994 | Bonutti et al. |
| 5,334,150 A | 8/1994 | Kaali |
| 5,356,421 A | 10/1994 | Castro |
| 5,376,076 A | 12/1994 | Kaali |
| 5,380,291 A | 1/1995 | Kaali |
| 5,431,151 A | 7/1995 | Riek |
| 5,431,676 A | 7/1995 | Dubrul et al. |
| 5,441,041 A | 8/1995 | Sauer |
| 5,445,142 A | 8/1995 | Hassler, Jr. |
| 5,467,762 A | 11/1995 | Sauer |
| 5,513,238 A | 4/1996 | Leber |
| 5,540,711 A | 7/1996 | Kieturakis |
| 5,551,947 A | 9/1996 | Kaali |
| 5,555,283 A | 9/1996 | Shiu |
| 5,562,696 A | 10/1996 | Nobles |
| 5,569,160 A | 10/1996 | Sauer |
| D377,093 S | 12/1996 | Michelson |
| 5,591,192 A | 1/1997 | Privitera |
| 5,609,562 A | 3/1997 | Kaali |
| 5,658,236 A | 8/1997 | Sauer |
| 5,662,111 A | 9/1997 | Cosman |
| 5,665,072 A | 9/1997 | Yoon |
| 5,676,673 A | 10/1997 | Ferre |
| 5,685,820 A | 11/1997 | Riek |
| 5,702,761 A | 12/1997 | DiChiara, Jr. |
| 5,738,628 A | 4/1998 | Sierocuk |
| 5,748,703 A | 5/1998 | Cosman |
| 5,748,767 A | 5/1998 | Raab |
| 5,762,629 A | 6/1998 | Kambin |
| 5,778,043 A | 7/1998 | Cosman |
| 5,782,807 A | 7/1998 | Falvai |
| 5,785,648 A | 7/1998 | Min |
| 5,792,044 A | 8/1998 | Foley |
| 5,800,352 A | 9/1998 | Ferre |
| 5,803,089 A | 9/1998 | Ferre |
| 5,829,444 A | 11/1998 | Ferre |
| 5,848,967 A | 12/1998 | Cosman |
| 5,860,996 A | 1/1999 | Urban et al. |
| 5,873,822 A | 2/1999 | Ferre |
| 5,902,272 A * | 5/1999 | Eggers et al. ............... 604/114 |
| 5,921,992 A | 7/1999 | Costales |
| 5,947,981 A | 9/1999 | Cosman |
| 5,967,970 A * | 10/1999 | Cowan et al. ............... 600/207 |
| 5,967,980 A | 10/1999 | Ferre |
| 5,971,997 A | 10/1999 | Guthrie |
| 6,005,919 A | 12/1999 | Kooy |
| 6,006,126 A | 12/1999 | Cosman |
| 6,007,481 A | 12/1999 | Riek |
| 6,041,101 A | 3/2000 | Kooy |
| 6,047,218 A | 4/2000 | Whayne et al. |
| 6,083,191 A | 7/2000 | Rose |
| 6,093,145 A | 7/2000 | VomBerg |
| 6,096,038 A | 8/2000 | Michelson |
| 6,120,465 A | 9/2000 | Guthrie |
| 6,129,685 A | 10/2000 | Howard, III |
| 6,142,931 A | 11/2000 | Kaji |
| 6,156,054 A | 12/2000 | Zadno-Azizi |
| 6,167,295 A | 12/2000 | Cosman |
| 6,175,756 B1 | 1/2001 | Ferre et al. |
| 6,179,826 B1 | 1/2001 | Aebischer |
| 6,214,017 B1 | 4/2001 | Stoddard |
| 6,221,078 B1 | 4/2001 | Bylsma |
| 6,224,599 B1 | 5/2001 | Baynham |
| 6,245,052 B1 * | 6/2001 | Orth et al. ............... 604/506 |
| 6,256,859 B1 | 7/2001 | Stoddard |
| 6,259,943 B1 | 7/2001 | Cosman |
| 6,275,725 B1 | 8/2001 | Cosman |
| 6,277,069 B1 | 8/2001 | Gray |
| 6,278,766 B1 | 8/2001 | Kooy |
| 6,283,912 B1 | 9/2001 | Hu |
| 6,293,952 B1 | 9/2001 | Brosens et al. |
| 6,296,647 B1 | 10/2001 | Robioneck |
| 6,331,180 B1 | 12/2001 | Cosman et al. |
| 6,341,231 B1 | 1/2002 | Ferre |
| 6,351,661 B1 | 2/2002 | Cosman |
| 6,359,959 B1 | 3/2002 | Butler |
| 6,371,964 B1 | 4/2002 | Vargas |
| 6,374,135 B1 | 4/2002 | Bucholz |
| 6,383,191 B1 | 5/2002 | Zdeblick |
| 6,405,072 B1 | 6/2002 | Cosman |
| 6,409,686 B1 | 6/2002 | Guthrie |
| 6,416,520 B1 | 7/2002 | Kynast et al. |
| 6,425,859 B1 | 7/2002 | Foley |
| 6,445,944 B1 | 9/2002 | Ostrovsky |
| 6,459,769 B1 | 10/2002 | Cosman |
| 6,461,330 B1 | 10/2002 | Miyagi |
| 6,478,806 B2 | 11/2002 | McFarlane |
| 6,551,240 B2 | 4/2003 | Henzler |
| 6,565,574 B2 | 5/2003 | Michelson |
| 6,589,211 B1 | 7/2003 | MacLeod |
| 6,595,917 B2 | 7/2003 | Nieto |
| 6,596,008 B1 | 7/2003 | Kambin |
| 6,599,292 B1 | 7/2003 | Ray |
| 6,602,227 B1 | 8/2003 | Cimino |
| 6,605,036 B1 | 8/2003 | Wild |
| 6,654,999 B2 | 12/2003 | Stoddard |
| 6,662,036 B2 | 12/2003 | Cosman |
| 6,669,685 B1 | 12/2003 | Rizoiu et al. |
| 6,675,040 B1 | 1/2004 | Cosman |
| 6,685,630 B2 | 2/2004 | Sauer |
| 6,761,687 B1 | 7/2004 | Doshi |
| D495,053 S | 8/2004 | Laun |
| 6,863,674 B2 | 3/2005 | Kasahara |
| 6,896,680 B2 | 5/2005 | Michelson |
| 6,942,634 B2 | 9/2005 | Odland |
| 7,081,089 B2 | 7/2006 | Bonadio |
| 7,153,304 B2 | 12/2006 | Robie |
| 7,235,084 B2 | 6/2007 | Skakoon |
| 7,474,820 B2 | 1/2009 | Vayser |
| 7,510,524 B2 | 3/2009 | Vayser |
| 7,686,492 B2 | 3/2010 | Vayser |
| 8,386,052 B2 | 2/2013 | Harris |
| 8,409,083 B2 | 4/2013 | Mangiardi |
| 8,608,650 B2 | 12/2013 | Mangiardi |
| 8,608,769 B2 | 12/2013 | Kahle |
| 8,679,088 B2 | 3/2014 | Abrahams |
| 2001/0010002 A1 | 7/2001 | Michelson |

(56) References Cited

U.S. PATENT DOCUMENTS

| | | | |
|---|---|---|---|
| 2001/0027271 A1 | 10/2001 | Franck | |
| 2002/0151769 A1 | 10/2002 | Kim | |
| 2002/0161366 A1 | 10/2002 | Robie | |
| 2003/0040753 A1 | 2/2003 | Daum | |
| 2003/0073934 A1* | 4/2003 | Putz | 600/585 |
| 2003/0139648 A1* | 7/2003 | Foley et al. | 600/114 |
| 2003/0145865 A1 | 8/2003 | Sterman | |
| 2004/0024291 A1 | 2/2004 | Zinkel | |
| 2004/0059375 A1 | 3/2004 | Ginn et al. | |
| 2004/0068172 A1 | 4/2004 | Nowinski et al. | |
| 2004/0097792 A1 | 5/2004 | Moll | |
| 2004/0102804 A1 | 5/2004 | Chin | |
| 2004/0186346 A1 | 9/2004 | Smith | |
| 2004/0230100 A1 | 11/2004 | Shluzas | |
| 2005/0273132 A1 | 12/2005 | Shluzas | |
| 2005/0277811 A1 | 12/2005 | Richards | |
| 2006/0041270 A1 | 2/2006 | Lenker | |
| 2006/0122462 A1 | 6/2006 | Roth | |
| 2006/0287583 A1 | 12/2006 | Mangiardi | |
| 2007/0232874 A1* | 10/2007 | Ince | 600/320 |
| 2008/0109026 A1 | 5/2008 | Kassam | |
| 2008/0119693 A1 | 5/2008 | Makower | |
| 2009/0312611 A1 | 12/2009 | Mangiardi | |
| 2010/0010315 A1 | 1/2010 | Mangiardi | |
| 2012/0071748 A1 | 3/2012 | Mark | |
| 2012/0253375 A1 | 10/2012 | Mark | |
| 2012/0289816 A1 | 11/2012 | Mark | |
| 2013/0066154 A1 | 3/2013 | Mangiardi | |
| 2013/0102851 A1 | 4/2013 | Mark | |
| 2013/0102886 A1 | 4/2013 | Mark | |
| 2013/0204095 A1 | 8/2013 | Mark | |
| 2013/0204287 A1 | 8/2013 | Mark | |
| 2014/0107426 A1 | 4/2014 | Wilson | |
| 2014/0187922 A1 | 7/2014 | Mark | |

FOREIGN PATENT DOCUMENTS

| | | |
|---|---|---|
| JP | 9224943 | 9/1997 |
| JP | 2000287915 | 10/2000 |
| JP | 2003153907 | 5/2003 |
| RU | 45928 | 6/2005 |
| RU | 55570 | 8/2006 |
| SU | 131027 | 3/1959 |
| SU | 349136 | 9/1972 |
| SU | 585840 | 1/1978 |
| SU | 1521465 | 11/1989 |
| WO | 0143627 | 6/2001 |
| WO | 2006017507 | 2/2006 |
| WO | 2006050047 | 5/2006 |
| WO | 2006050225 | 11/2006 |
| WO | 2013063027 | 5/2013 |
| WO | 2014137530 | 9/2014 |
| WO | 2014137551 | 9/2014 |

OTHER PUBLICATIONS

H. Gumprecht, H.A. Trost & C.B. Lumenta; "Neuroendoscopy combined with frameless neuronavigation"; British Journal of Neurosurgery 2000; vol. 14 (2); pp. 129-131.
Office Action mailed Jul. 27, 2015 for U.S. Appl. No. 13/674,507.
Office Action mailed Jul. 7, 2015 for U.S. Appl. No. 14/134,360.
Alberti, O., et al., "Frameless navigation and endoscopy," Journal of Neurosurgery, 2001, Sep; 95(3): 541-3. Abstract only.
Alexander, et al. "Chapter 20: Stereotactic Frame Systems: The COMPASS System," Advanced Neurosurgical Navigation, 1999, pp. 267-277. 13 pages.
Amstutz, C., et al., "A-Mode Ultrasound-Based Registration in Computer-Aided Surgery of the Skull," Arch Otolaryngol Head Neck Surg. 2003; 129 (12):1310-1316.
Andrews, R.J., et al., "A review of brain retraction and recommendations for minimizing intraoperative brain injury," Neurosurgery 1993; 33(6): 1052-1063.
Burtscher, J., et al., "Neuroendoscopy Based on Computer Assisted Adjustment of the Endoscope Holder in the Laboratory.," Minimum Invasive Neurosurgery 2003; 46:208-214.
Decision for Rejection for Patent Application No. 2009-539227 dated May 31, 2013.
Eldeib, A.M., et al., "Rigid neuroendoscope navigation system for minimally invasive surgery," Engineering in Medicine and Biology, 1999. Abstract only.
Engh, et al. NeuroendoportSM surgery facilitates removal of hard-to-reach brain tumors, University of Pittsburgh Neurosurgery News, vol. 10, No. 2, 2009. 8 pages.
Entire patent prosecution history of U.S. Appl. No. 11/155,175, filed Jun. 17, 2005, entitled, "Surgical Access Instruments for Use With Delicate Tissues."
Entire patent prosecution history of U.S. Appl. No. 12/545,686, filed Aug. 29, 2009, entitled, "Surgical Access Instruments for Use With Delicate Tissues."
Entire patent prosecution history of U.S. Appl. No. 13/431,280, filed Mar. 27, 2012, entitled, "Tissue Retractor Apparatus and Methods."
Entire patent prosecution history of U.S. Appl. No. 13/674,507, filed Nov. 12, 012, entitled, "Tissue Retractor Apparatus and Methods."
Extended European Search Report for EP 08 840 022.5, The Hague, Mar. 18, 2013.
Fukamachi, A., et al., "Postoperative intracerebral hemorrhages: a survey of computed tomographic findings after 1074 intracranial operations," Surgery Neurol 1985; 23(6); 575-580. Abstract only.
Greenfield, et al. "Stereotactic Minimally Invasive Tubular Retractor System for Deep Brain Lesions," Operative Neurosurgery 2, vol. 63, Oct. 2008, pp. 334-340. 7 pages.
Greenfield, JP, et al., "Stereotactic minimally invasive tubular retractor system for deep brain lesions," Neurosurgery 2008; 63(4): 334-339. Abstract only.
Hellwig, D., et al. "Neuroendoscopic Treatment for Colloid Cysts of the Third Ventricle: The Experience of a Decade," Neurosurgery, Mar. 2003; 52(3):525-533. Abstract only.
Hilton et al., "METRx Microdiscectomy Surgical Technique," Medtronic Sofamor Danek publication, 2001, 20 pages.
International Preliminary Report on Patentability and Written Opinion for International Application No. PCT/US2006/061246 dated Jun. 3, 2009.
K043602 510(k) Summary, Feb. 23, 2005.
K060973 510(k) Summary, Jul. 26, 2006.
Kelly, et al. "The stereotaxic retractor in computer-assisted stereotaxic microsurgery," Journal of Neurosurgery, vol. 69, Aug. 1988, pp. 301-307, 7 pages.
Konen, W., et al., "An Image-Based Navigation Support System for Neuroendoscopic surgery," R. Ahlers (ed.) 5. Symposium Bilderarbeitung 1997, Technische Akademie Essingen. pp. 1-8.
Kubo, S., et al., "A Newly Designed Disposable Introducer Sheath for a Ventricular Fiberscope," Minimum Invasive Neurosurgery 2004; 47(2): 124-126. Abstract only.
Lemole, G.M., et al., "Cranial Application of Frameless Stereotaxy," Barrow Neuological Institute 2001; 17(1): 1-12.
McInerney, J., et al., "Frameless Stereotaxy of the Brain," The Mount Sinai Journal of Medicine 2000; 67(1): 300-310.
Mettler, L., et al., "Optical trocar systems: laparpscopic entry and its complications (a study of cases in Germany)," Gynaecological Endoscopy 1999; 8(6): 383-389. Abstract only.
Ogura, K., et al., "New microsurgical technique for intraparenchymal lesions of the brain: transcylincer approach," Aeta Neurochirurgica (Wien) 2006; 148: 779-785.
OShaughnessy, P., "New Brain tumor technology helps man who took two bullets to the head return to normal life," Daily News, Jun. 19, 2011.
Preliminary Amendment and Request for Interference for U.S. Appl. No. 14/134,360 dated Dec. 23, 2013.
Prevedello, et al. "Vycor ViewSite TC: Endoscope guided Intraparenchimal Brain Tumor Ressection," Ohio State University Medical Center Minimally Invasive Neurosurgery, 2 pages.
Rampini, P., et al., "Stereotactically guided endoscopy for the treatment of arachnoid cysts." Pediatric Neurosurgery 1998; 29(2): 102-104. Abstract only.

(56) References Cited

OTHER PUBLICATIONS

Raza. et al. "Minimally Invasive Trans-Portal Resection of Deep Intracranial Lesions," Minimally Invasive Neurosurgery, vol. 54, Feb. 2011, pp. 1-7.
Recinos, et al. "Use of a minimally invasive tubular retraction system for deep-seated tumors in pediatric patients," Journal of Neurosurgery: Pediatrics, vol. 7, May 2011, pp. 516-521. 6 pages.
Ross, D.A., "A simple stereotactic retractor for use with the Leksell stereotactic system," Neurosurgery 1993; 32(3): 475-476. Abstract only.
Scholz, M., et al., "Development of an Endoscopic Navigation System Based on Digital Image Processing," Computer Aided Surgery 1998; 3(3): 134-143. Abstract only.
Scholz, M., et al., "Virtual image navigation: a new method of control intraoperative bleeding in neuroendoscopic surgery," Neurosurg Focus 2000; 8(6): 1-8.
Shults, et al. "Neuro-Opthalmic Complications of Intracranial Catheters," Neurosurgery, vol. 33, No. 1, Jul. 1993, pp. 135-138. 4 pages.
Spetzger, U., et al., "Navigational microneurosurgery: experience with Easy Guide Neuro," Medicamundi 1997; 41(1): 28-35.
UPMC: Minimally Invasive Brain Surgery. Legacy of Innovations. Breakthroughs in minimally invasive brain surgery at UPMC. 2014.
Zhong, J., et al., "Brain retraction injury," Neurological Research 2003; 25: 831-838.
"Neuronavigation" from Wikipedia dated Jul. 30, 2014.
Entire patent prosecution history of U.S. Appl. No. 12/545,719, filed Aug. 21, 2009, entitled, "Surgical Access Methods for Use With Delicate Tissues," now U.S. Pat. No. 8,409,083, issued Apr. 2, 2013.
Entire patent prosecution history of U.S. Appl. No. 14/134,360, filed Dec. 9, 2013, entitled, "Apparatus and Methods for Performing Brain Surgery."
Slavin et al., "Testimonials," no date but admitted as prior art between Jun. 17, 2005 and Mar. 27, 2012.
Vycor Medical, "Vycor ViewSite TC: Endoscopic Intraparenchimal Brain Tumor Resection with Image Guidance," 2 pages, no date but admitted as prior art between Jun. 17, 2005 and Mar. 27, 2012.
Herrera, S. et al., "Use of Transparent Plastic Tubular Retractor in Surgery for Deep Brain Lesions: A Case Series," Surgical Technology International XIX, pp. 1-4, published in 2010.
International Search Report and Written Opinion for International Application No. PCT/US2015/030528 mailed Aug. 14, 2015.
Wang, W.H. et al., "Endoscopic hematoma evacuation in patients with spontaneous supratentorial intracerebral hemorrhage," Journal of the Chinese Medical Associations, vol. 78, 2015, pp. 101-107.
Tao, X. et al., "Microsurgical resection for lateral ventrical meningiomas with neuronavigatIon and tubular retractor system," Chin. J. Neurosurg, vol. 31, No. 4, 2015, pp. 332-336 (abstract only).
Rymarczuk, G.N. et al., "Use of a Minimally Invasive Retractor System for Retrieval of Intracranial Fragments in Wartime Trauma," World Neurosurgery, 2015, pp. 1-26.
Shoakazemi, A. et al., "A 3D endoscopic transtublar transcallosal approach to the third ventricle," J. Neurosurg, 2015, pp. 1-10.
Nagatani, K. et al., "High-Definition Exoscope System for Microneurosurgery: Use of an Exoscope in Combination with Tubular Retraction and Frameless Neuronavigation for Microsurgical Resection of Deep Brain Lesions," No Shinkei Geka, Jul. 2015, vol. 43, No. 7, pp. 611-7 (Abstract Only).
Nico Corporation Press Release, "NICO Corporation Gains Market Expansion after Multiple Published Clinical Articles Support Access Technology for Deep Brain Lesions," May 5, 2015, pp. 1-2.
Ding, D. et al., "Endoport-assisted microsurgical resection of cerebral cavernous malformations," J. Clin. Neurosci., Jun. 2015, vol. 22, No. 6, pp. 1025-9 (Abstract Only).
Del Ray Medical Center Press Release, "Advanced Neuroscience Network Brings New Innovations in Neurosurgery to South Florida," May 13, 2015, pp. 1-6.

\* cited by examiner

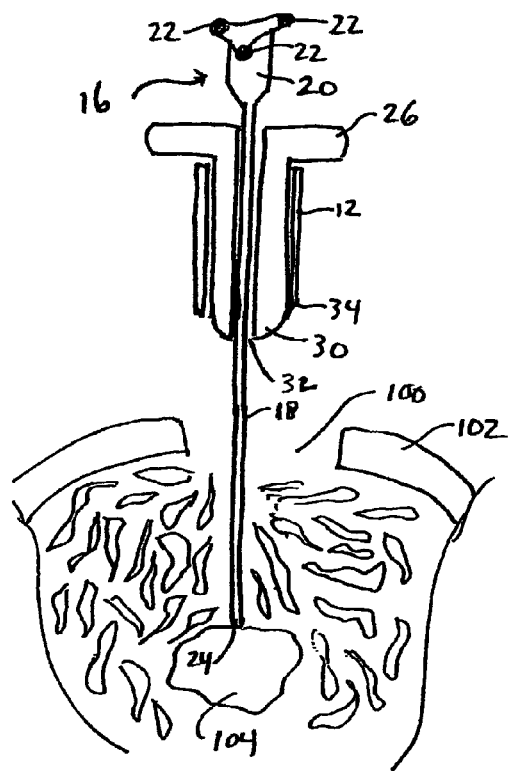
Fig 7
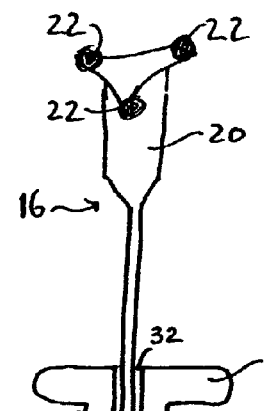
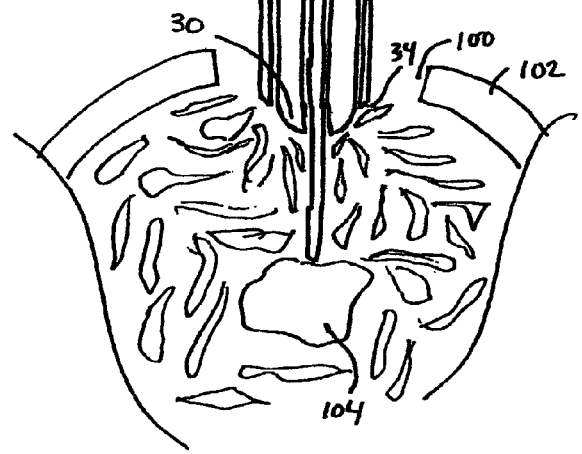
Fig 8

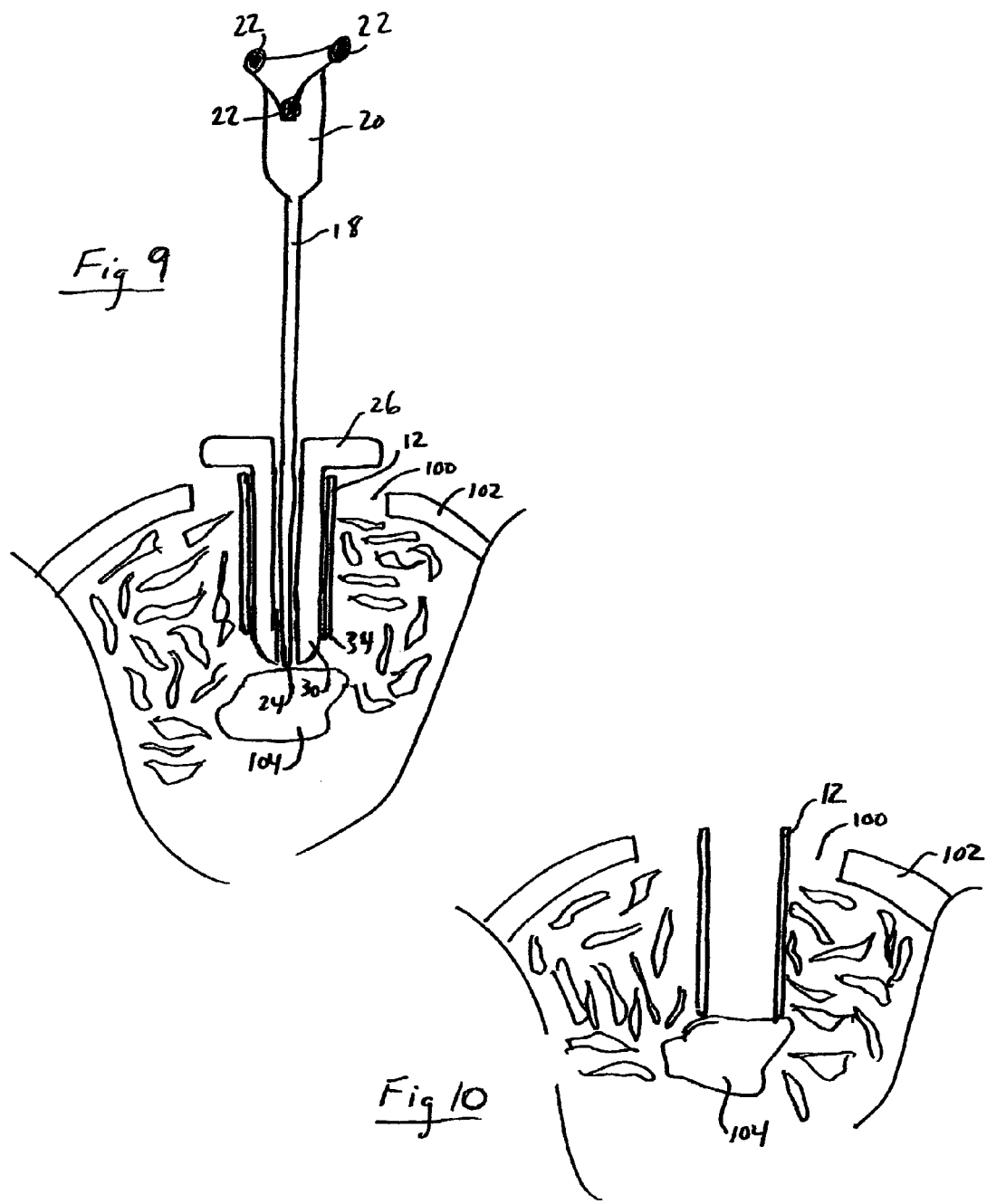

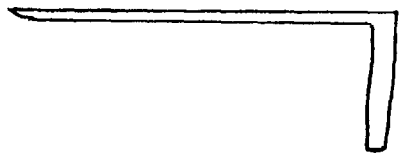
Fig. 21

APPARATUS AND METHODS FOR PERFORMING BRAIN SURGERY

PRIORITY

The present application claims the benefit of and priority to International Application No. PCT/US2005/038828 filed Oct. 28, 2005, claiming priority from U.S. Provisional Application Ser. No. 60/622,991 filed Oct. 28, 2004, the entire contents of each of which are incorporated herein by reference.

TECHNICAL FIELD

The present disclosure relates to methods of accessing and performing surgery within the brain.

BACKGROUND

Diagnosis and treatment of conditions affecting the brain are among the most difficult and complex problems that face the medical profession. The brain is a delicate soft tissue structure that controls bodily functions through a complex neural network connected to the rest of the body through the spinal cord. The brain and spinal cord are contained within and protected by significant bony structures, e.g., the skull and the spine. Given the difficulty of accessing the brain through the hard bony protective skull the diagnosis and treatment of brain disorders presents unique challenges not encountered elsewhere in the body.

Diagnosis of brain disorders requires clear, accurate imaging of brain tissue through the skull. In recent years significant advances have been made in imaging technology, including stereotactic X-ray imaging, Computerized Axial Tomography (CAT), Position Emission Tomography (PET) and Magnetic Resonance Imaging (MRI). See, for example, Butler U.S. Pat. No. 6,359,959. These imaging devices and techniques permit the surgeon to examine conditions within the brain in a non-invasive manner without opening the skull. If a target lesion or mass is identified through use of one or more imaging techniques, it may be necessary or desirable to biopsy a lesion within the brain. Stereotactic techniques and apparatus for directing a biopsy needle to the site are described and shown, for example, in Cosman U.S. Pat. Nos. 6,331,180 and 6,416,520.

Once a diagnosis has been reached based upon one or more imaging techniques, a treatment plan must be developed. One available method of treatment involves X-ray therapy such as disclosed in Leber U.S. Pat. No. 5,513,238; Shiu U.S. Pat. No. 5,555,283; Cosman U.S. Pat. Nos. 5,748,703, 5,778,043, 5,947,981, 6,459,769; and Kooy U.S. Pat. Nos. 6,005,919, 6,041,101, and 6,278,766. Alternatively, surgical treatment may be necessary or desired. In order to operate surgically on the brain, access must be obtained through the skull and delicate brain tissue containing blood vessels and nerves that can be adversely affected by slight disturbances. Therefore, great care must be taken in operating on the brain not to disturb delicate blood vessels and nerves so that adverse consequences do not result during or after surgery. Brain surgery can be highly invasive. In some instances, in order to obtain access to target tissue, a substantial portion of the skull is removed and entire sections of the brain are retracted to obtain access. Of course, such techniques are not appropriate for all situations, and not all patients are able to tolerate and recover from such invasive techniques. It is also known to access certain portions of the brain by forming a hole in the skull, but only limited surgical techniques may be performed through such smaller openings. In addition, some techniques have been developed to enter through the nasal passages, opening an access hole through the occipital bone to remove tumors located, for example, in the area of the pituitary.

A significant advance in brain surgery is stereotactic surgery involving a stereotactic frame correlated to stereotactic X-ray images to guide a probe or other surgical instrument through an opening formed in the skull through brain tissue to a target lesion or other body. See, for example, U.S. Pat. Nos. 6,331,180 and 6,416,520. A related advance is frameless image guidance, in which an image of the surgical instrument is superimposed on a pre-operative image to demonstrate the location of the instrument to the surgeon and trajectory of further movement of the probe or instrument. Image guided surgery is described, for example, in Guthrie U.S. Pat. Nos. 5,230,623, 5,971,997, 6,120,465, and 6,409,686; Cosman U.S. Pat. Nos. 5,662,111, 5,848,967, 6,006,126, 6,167,295, 6,259,943, 6,275,725, 6,351,661, 6,405,072, 6,662,036, and 6,675,040; and Faro U.S. Pat. Nos. 5,251,127, 5,305,203, and 5,748,767.

Kassam published U.S. patent application 2008/0109026 proposes alternate methods and devices for performing brain surgery involving inserting a cannula with a dilating obturator into the brain to gently dilate the brain tissue. The cannula and dilating obturator may be inserted under image guidance. The cannula provides access to tissue within the brain and provides a working space for the surgeon to perform surgery on structures of the brain, preferably using an endoscope partially inserted into the cannula to visualize the operative site at the end of the cannula. The image from the endoscope may be projected onto a monitor or screen to assist the surgeon and others to visualize the structures of the brain. The present disclosure provides alternative structures and techniques useful in performing surgery in accordance with the techniques disclosed, described or shown in the foregoing application.

Dubrul U.S. Pat. Nos. 5,183,464 and 5,431,676 disclose and describe expandable dilators or trocars useful for accessing hollow body organs. Structures similar to those described by Dubrul have been marketed and sold for laparoscopic access under the trademark STEP by Innerdyne, Inc., and subsequently by the AutoSuture Division of Tyco Healthcare Group, LP (Norwalk, Conn.). Expandable cannula structures having longitudinal wire also are disclosed and described in Bonutti U.S. Pat. No. 5,320,611.

Urban U.S. Pat. No. 5,860,996 discloses and describes an optical trocar for use in laparoscopic surgical procedures. The optical trocar includes a movable cutting blade extendable from a rounded optical window at the distal tip as penetration through tissue is observed through an endoscope inserted into a sleeve until the tip of the endoscope is adjacent to the window. Optical trocars have been marketed for laparoscopic access under the trademark VISIPORT by the AutoSuture Division of Tyco Healthcare Group, LP (Norwalk, Conn.). Penetrating optical trocars also are shown and described in Kaali U.S. Pat. Nos. 5,334,150, 5,376,076, 5,380,291, 5,551, 947, 5,609,562, and 5,702,761; Sauer U.S. Pat. Nos. 5,441, 041, 5,467,762, 5,569,160, and 6,685,630; Reik U.S. Pat. Nos. 5,271,380, 5,431,151, 5,685,820, and 6,007,481; and Hassler U.S. Pat. No. 5,445,142.

SUMMARY OF THE DISCLOSURE

Apparatus and methods are disclosed for atraumatically dilating brain tissue to access target tissue within the brain.

A first apparatus for accessing brain tissue has a dilating obturator with a blunt rounded distal tip, a substantially cylindrical shaft portion, and a proximal handle portion. A cannula is disposed around the shaft portion and preferably is made of a transparent material. The obturator and cannula assembly preferably is associated with an image-guided surgery system so that placement of the obturator and cannula assembly can be carefully monitored and controlled as the obturator and cannula assembly is atraumatically inserted into brain tissue.

In a first embodiment of such an apparatus the obturator has a longitudinal channel therethrough configured and dimensioned to receive the shaft of a narrow stylet or probe. The stylet or probe has attached thereto image guidance means calibrated to indicate the orientation and position of the stylet or probe. An image guidance system interacts with the stylet or probe to display for the surgeon on a monitor an image of the stylet or probe superimposed onto an image of the patient s brain, such as an MRI image. The image may be a pre-operative MRI image used for surgical planning. When the stylet or probe is mounted in the longitudinal channel of the obturator, the superimposed image of the probe also is indicative of the position and orientation of the dilating obturator and the cannula.

Traditional methods are used to incise and retract soft tissue of the scalp covering the skull. A hole is made in the skull, and the dura is opened and retracted to provide access to the brain. The stylet or probe is inserted through the obturator longitudinal channel and advanced until a length of the stylet or probe extends out of and beyond the blunt rounded tip of the dilating obturator. The dilating obturator and cannula assembly is held back away from the tissue as the stylet or probe is gently advanced through the brain tissue under both direct vision and positional image guidance until the tip of the stylet or probe is adjacent the target tissue. Once the stylet or probe is placed and the position is confirmed using the image guidance system, the blunt rounded dilating obturator and cannula assembly is slowly and carefully advanced into the brain tissue to atraumatically spread the tissue over the dilating tip and around the cannula while maintaining the position of the stylet or probe as a guide to advancement of the obturator and cannula assembly. A gentle back and forth rotation during insertion may facilitate placement of the obturator and cannula assembly. Once the dilating obturator and cannula assembly are correctly positioned adjacent the target tissue, the stylet or probe and dilating obturator are removed, leaving the cannula in place to support and protect the dilated brain tissue. Preferably, the cannula is clear so that the dilated brain tissue may be visually inspected through the walls of the cannula to assure that no damage was caused to surrounding brain tissue during insertion of the device.

Alternatively, in a second contemplated embodiment of such an apparatus the image guidance means may be mounted directly to the dilating obturator and cannula assembly so that the obturator and cannula assembly may be inserted without a separate stylet or probe. In this configuration, the obturator and cannula assembly is inserted into the brain tissue under image guidance until the obturator is adjacent the target tissue. Once the obturator and cannula assembly is positioned, the dilating obturator is removed, leaving the cannula in place.

In yet a third contemplated embodiment of such an apparatus, the dilating obturator and cannula assembly may be inserted into the brain under direct visualization without use of an image guidance system.

In yet a fourth alternative embodiment a tissue dilator has an optical window at the tip thereof and is configured and dimensioned to receive an endoscope or like device such that the user may visualize brain tissue as the dilator is inserted directly into the brain. The optical dilator is surrounded by a cannula, and may optionally also have a longitudinal channel to receive a stylet or probe. The optical dilating obturator and cannula assembly may be inserted into the brain under direct visualization, and progress through brain tissue may be observed during insertion either directly through the endoscope or by projecting the image from the endoscope onto a monitor or screen. The optical dilator and cannula assembly may be provided with identifying indicia compatible with an image guidance system such that the optical dilating obturator and cannula may be inserted utilizing both visualization of brain tissue and image guidance. Alternatively, the optical dilator may be provided with an auxiliary channel configured and dimensioned to receive a stylet or obturator, such that the stylet may be inserted into the brain to the target tissue under image guidance, with the optical obturator used to visualize the brain tissue as the optical obturator and cannula assembly is inserted over the stylet to reach the target tissue. After the optical obturator and cannula assembly is inserted to the desired location the optical dilator, stylet (if used) and endoscope may be removed, leaving the cannula in place to provide access and a working space to the surgeon. The same or another endoscope may thereafter be mounted partially extending through the cannula to provide visualization of the target tissue at the end of the cannula for surgery. Alternatively, optics may also be incorporated directly into the optical dilator, or an endoscope may be inserted through the cannula such that the endoscope acts as the dilator.

After the cannula is placed, surgery may be performed through the cannula, either under direct vision or more preferably using an endoscope and camera system to project an enlarged image of the target tissue onto a monitor to visualize the tissue during surgery.

Preferably, the cannula has a diameter of approximately 10 mm to 20 mm, and more preferably 10 mm to 15 mm. An endoscope of a substantially smaller diameter, such as a 4 mm endoscope, is mounted partially inserted into the cannula. The endoscope is mounted to one side of the cannula and inserted so that the image projected onto the monitor is of the target tissue at the end of the cannula. In practice, a 4 mm endoscope is inserted approximately halfway into the cannula is appropriate to create the desired image display while leaving a substantial portion of the cannula open and available for the insertion of instruments to perform surgery. Optionally, a camera holder may be used to secure the endoscope in the desired position.

Appropriate surgical instruments are then used to perform surgery upon the target tissue. For example, scissors, graspers and suction tools may be inserted through the cannula, visualizing the tips of the instruments to perform the desired procedure either directly with the naked eye or through a microscope, or indirectly through the endoscope using the endoscope eyepiece or more preferably and camera system to display the image on a monitor. A preferred instrument for debulking brain tissue is a fluidized ultrasonic instrument, such as CUSA (Valleylab, Boulder Colo.). Monitoring equipment may be used to monitor brain function during surgery to assist the surgeon in understanding the effects of the actions taken during surgery on the brain so that the surgery may be terminated in the event an indication of an adverse effect is detected.

After surgery upon the target tissue is complete, the cannula is gently removed, and the dura, skull and scalp are closed in a traditional fashion.

In an alternative apparatus, a stylet or probe is inserted into the brain, preferably under image guidance, until the tip of the probe is adjacent target tissue within the brain. The stylet is surrounded by an expandable sleeve extending substantially the entire length of the stylet or probe which is inserted into the brain together with the stylet or probe. An expanding dilator and cannula assembly is then inserted into the expandable sleeve to atraumatically expand the sleeve to the diameter of the cannula, thereby atraumatically dilating the brain tissue surrounding the expandable sleeve to accommodate the cannula. In one such embodiment, the dilator and cannula assembly is inserted over the stylet with the stylet extending through a longitudinal passage provided for that purpose through the dilator. Alternatively, it is contemplated that the stylet or probe may be removed prior to inserting the dilator and cannula assembly, such that the expandable sleeve remains as placed in the brain using the stylet, ready to receive and guide the dilator and cannula assembly. The expandable sleeve may be attached to a hub, with the cannula and dilator inserted through the hub into the expandable sleeve. Alternative variations of the dilating tip and cannula are contemplated. By way of example only, the dilating obturator may have a blunt conical tip or a semi-spherical, curved or other outer surface configured to expand the expandable sleeve to the diameter of the cannula without requiring undue force or traumatizing surrounding tissue. A substantially flat or slightly curved tip surface may suffice depending upon the ratio of the unexpanded sleeve to the cannula diameter.

In a further alternative embodiment, it is contemplated that a radially dilating structure may be used rather than a dilator that utilizes longitudinal insertion to expand the sleeve. In one radially expandable configuration segments of cannula wall are moved into a configuration to define a cannula, and may become self-supporting in such configuration or may be locked into such position by one or more locking elements.

Another radial expansion device involves a braid structure that is compressed so that the resulting decrease in braid angle causes the tubular or other shaped braid to expand. Such a radially expanding braid may be used to expand the expandable sleeve or may be incorporated directly into and become part of the expandable sleeve.

In yet a further alternative embodiment the cannula is inserted into the expandable sleeve without a dilating obturator.

In yet a further alternative embodiment the dilating obturator to be inserted into the expandable sleeve may have a clear or transparent window at the tip, with a longitudinal channel configured and dimensioned to receive an endoscope. In this manner, as the dilator is inserted through the expandable sleeve, the surgeon may view the brain tissue being dilated, and may immediately visualize the target tissue after the dilating tip has been inserted to the desired depth. The optical dilator may optionally include a longitudinal channel to receive the stylet or probe.

In all of the contemplated embodiments, the surgeon is provided with a cannula which is atraumatically inserted and which atraumatically retracts brain tissue to provide access and working space sufficient to allow the surgeon to perform surgery on the target brain tissue. While the cannula is shown and described as cylindrical, it is also contemplated that the cannula may have a non-circular cross-section, such as square, rectangular, elliptical, oval or other shape as may be necessary or desirable under particular circumstances.

The devices and methods disclosed herein provide numerous advantages in performing brain surgery. Gentle atraumatic dilation of the brain tissue makes it possible to operate further inside the brain than otherwise would be possible utilizing traditional surgical techniques. The disclosed methods and apparatus create an access area to work while simultaneously protecting adjacent brain tissue from inadvertent collateral damage and trauma that might otherwise occur if more traditional surgical techniques were to be utilized. In addition, accessing target tissue through the cannula as contemplated avoids more invasive techniques that involve removing substantial portions of the skull and retracting large portions of the brain to gain access to operate on target tissues. In some cases, the devices and methods may make it possible to operate on target tissue that would, without these devices and methods, otherwise be regarded as inoperable using previously known techniques.

BRIEF DESCRIPTION OF THE DRAWINGS

The accompanying drawings form a part of this disclosure, in which:

FIG. 7 is an illustration of the first embodiment with the stylet inserted to a point adjacent target tissue within the brain;

FIG. 8 is an illustration of the first embodiment with the obturator and cannula assembly partially inserted into and atraumatically separating brain tissue;

FIG. 9 is an illustration of the first embodiment, with the obturator and cannula assembly inserted over the stylet to target tissue;

FIG. 10 is an illustration of a cannula in place holding brain tissue apart to provide access to target tissue;

FIG. 14A is a proximal end view of the expandable sleeve and hub assembly;

FIG. 21 is a cross section view of a cannula including a proximal annular flange.

DETAILED DESCRIPTION OF THE PREFERRED EMBODIMENTS

Figure 1:
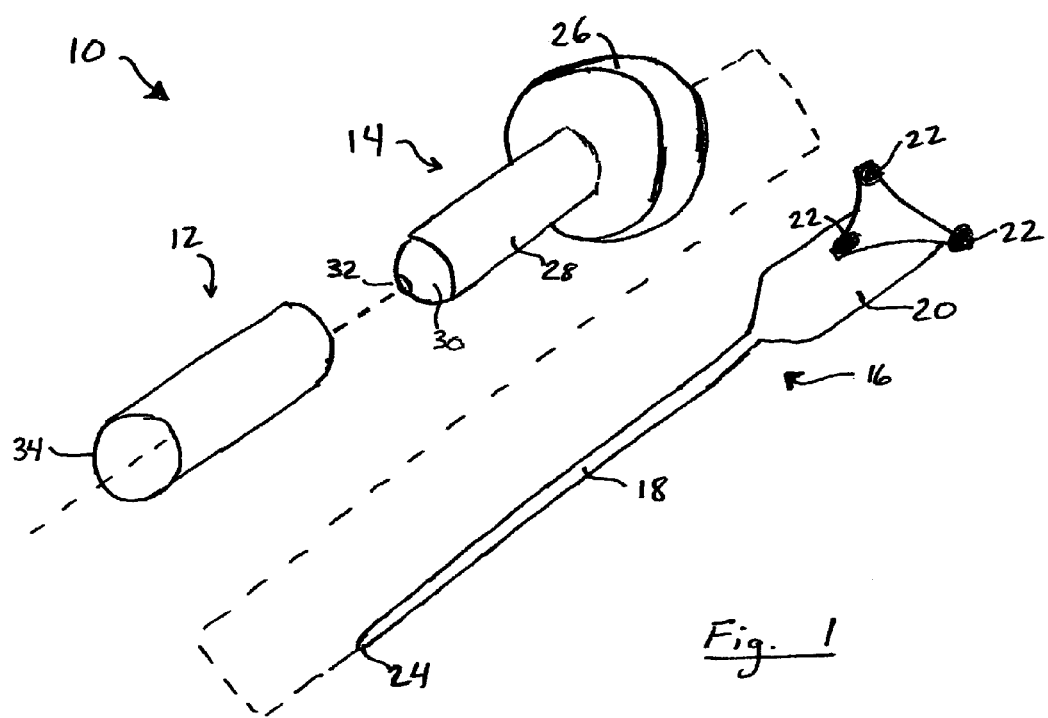
FIG. 1 is a perspective view, with parts separated, of an access device in accordance with a first embodiment.

Referring now to the drawings, FIG. 1 illustrates a first embodiment of an apparatus 10 for accessing target tissue within the brain in order to perform brain surgery. The access device includes a cannula 12, a dilating obturator 14 and a stylet or probe 16. Stylet or probe 16 has a small diameter elongated shaft 18, a handle 20 and associated position indicators 22 for a position guidance system. Stylet shaft 18 has a blunt tip 24 that can be inserted into and advanced through brain tissue. In FIG. 1, image guidance position indicators are shown as infrared reflectors of the type use in connection with optical image guidance systems, although other position indicating systems could be used. As shown, the infrared reflectors used with such a system are mounted to the stylet handle in a customary triangular configuration calibrated to identify the tool to the image guidance system. Such imaging systems are available, for example Medtronic Surgical Navigation Technologies (Denver, Colo.), Stryker (Kalamazoo, Mich.), and Radionics (Burlington Mass.).

Typically, the positioning of the indicator reflector balls is calibrated such that the image guidance system recognizes the particular tool and projects an image of the tool onto a display of images of the patient s brain, such as MRI images used to plan surgery. Calibration of instruments to an image guidance system is disclosed, for example, in Costales U.S. Pat. No. 5,921,992. As the instrument is inserted, the surgeon can see the relative position of the instrument relative to the structures of the brain as reflected on images used to plan surgery, particularly with respect to the target tissue.

Dilating obturator 14 has a proximal handle portion 26, a substantially cylindrical shaft portion 28, and a blunt dilating tip 30. Blunt dilating tip 30 is of a rounded atraumatic configuration, such as a semi-spherical dome or other gently curved surface. A longitudinal access channel 32 extends through the dilating obturator 14. The longitudinal channel is configured and dimensioned to receive shaft 18 of the stylet or probe 16. Cannula 12 is substantially cylindrical and is configured to slide over and mount onto the substantially cylindrical shaft 28 of the dilating obturator 14. Leading edge 34 of cannula 12 may be chamfered to reduce insertion force and minimize trauma during insertion into the brain.

Figure 2:
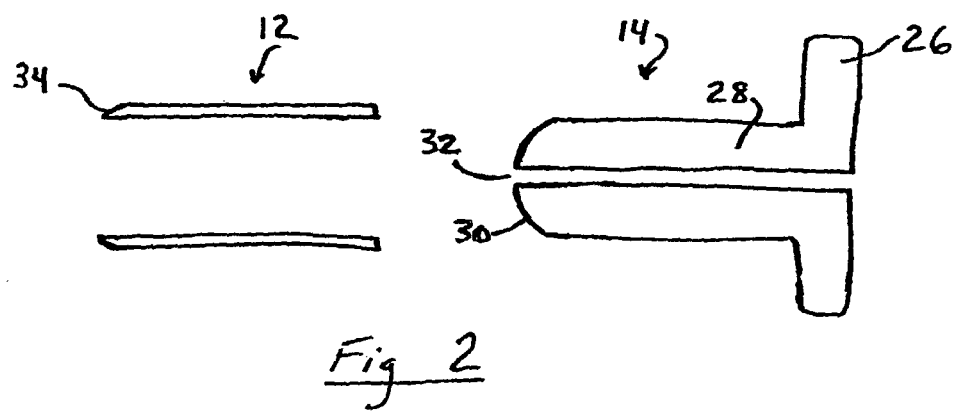
FIG. 2 is a cross-sectional view of an obturator and cannula assembly, with parts separated, in accordance with the first embodiment.

FIG. 2 is a cross-section view of the cannula 12 and dilating obturator 14 of the first embodiment, illustrating blunt rounded dilating tip 30 of the dilating obturator 14, the chamfered lead edge 34 of cannula 12 and the longitudinal access channel 32 extending axially through the entire length of the dilating obturator.

Figure 3:
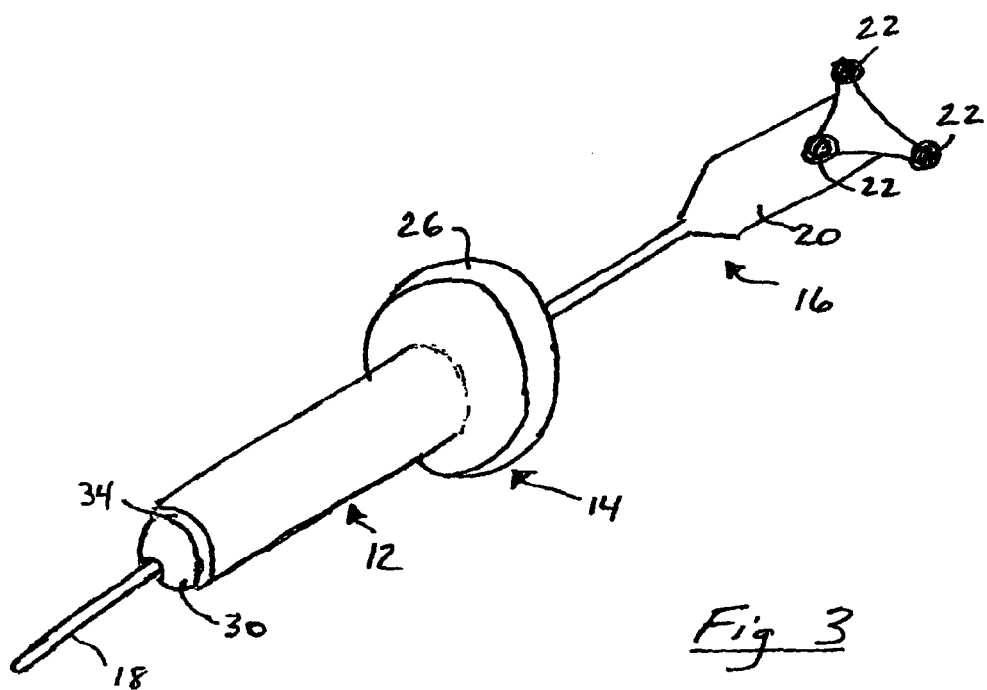
FIG. 3 is a perspective view of an obturator, cannula and stylet assembly in accordance with the first embodiment.

FIG. 3 is a perspective view of the first embodiment in an assembled condition, with cannula 12 disposed over the shaft of dilating obturator 14 and stylet or probe shaft 18 inserted through the longitudinal access channel 32 of the dilating obturator. Stylet 18 is shown projecting from the distal, rounded tip of the dilating obturator.

Figure 4:
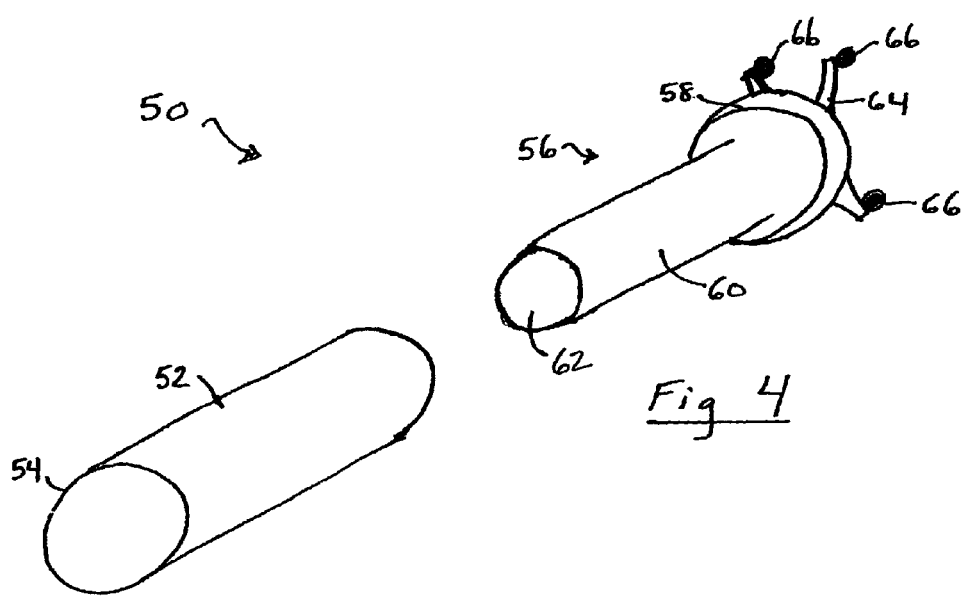
FIG. 4 is a perspective view, with parts separated, of an access device in accordance with a second embodiment.

FIG. 4 is a perspective view, with parts separated, of a second embodiment of an access device 50 for brain surgery. Access device 50 includes a cannula 52 with a chamfered lead edge 54. Access device 50 also includes a dilating obturator 56 having a handle portion 58, a substantially cylindrical shaft 60 and an atraumatic blunt dilating tip 62. Blunt tip 62 has a rounded distal surface, such as a semi-spherical surface. Cannula 52 is configured and dimensioned to mount over shaft 60 of the dilating obturator. The obturator shaft is configured and dimensioned to removably fit into the cannula inner diameter and to occupy the open space within the cannula. As shown in FIG. 4, the image guidance identification device 64 with infrared imaging reflectors 66 is attached directly to the dilating obturator, eliminating the stylet or probe of the first embodiment. Accordingly, the dilating obturator of the second embodiment also need not include the longitudinal access channel for the stylet or probe.

For illustration purposes devices disclosed herein are shown with infrared reflectors as used with available optical image guidance systems. Other guidance systems, such as magnetic or electromagnetic or radio transmitting systems may also be used, and the illustration of infrared reflectors and discussion of optical image guidance systems are exemplary only and are not intended to be limiting. In addition, currently available image guidance systems superimpose an image of the tool onto a pre-operative image. It is contemplated that as technology continues to progress that real-time imaging capability may become available in the operating room, and that the image of the tool may then be shown in relation to the surrounding tissue structures on a real time image.

Figure 5:
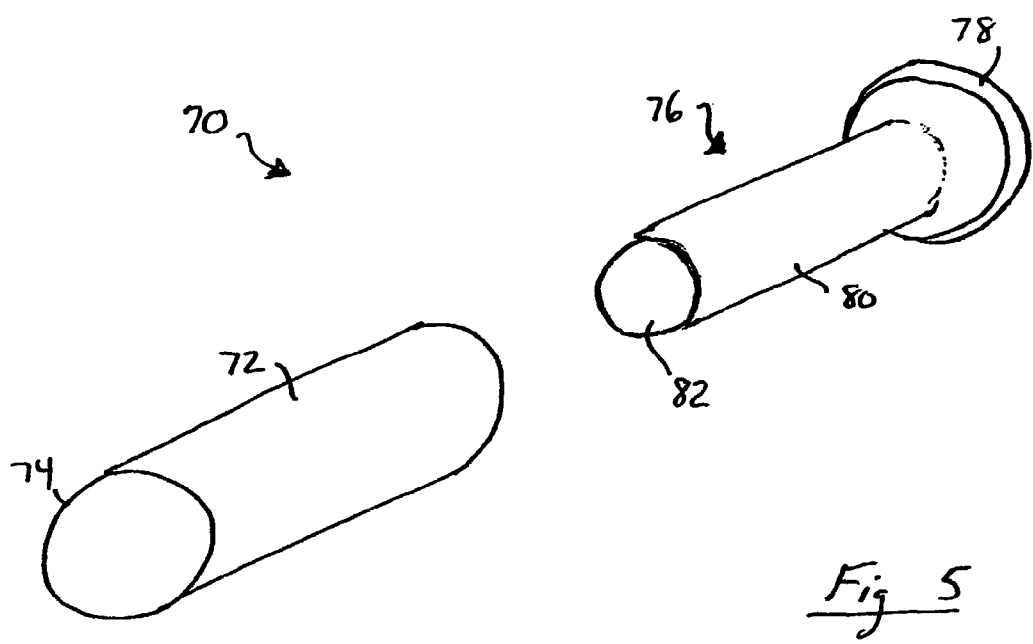
FIG. 5 is a perspective view, with parts separated, of an access device in accordance with a third embodiment.

FIG. 5 is a perspective view, with parts separated, of a third embodiment of an access device 70 for brain surgery. Access device 70 includes cannula 72 with chamfered lead edge 74, and a dilating obturator 76. Dilating obturator 76 includes a handle 78, substantially cylindrical shaft 80 and rounded dilating tip 82, which may be semi-spherical. Access device 70 does not include apparatus for calibrating the position of the dilating obturator with an image guidance system or a stylet or probe for aiding insertion of the dilating obturator.

Figure 6A:
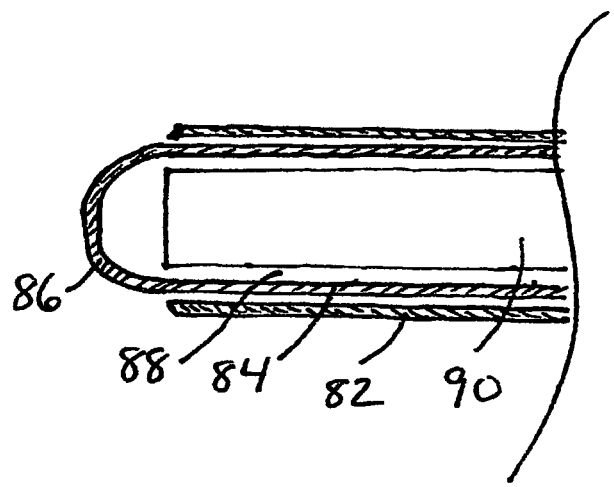
FIG. 6A is a partial cross-section view of a first optical dilator with an endoscope disposed in the optical dilator.
Figure 6B:
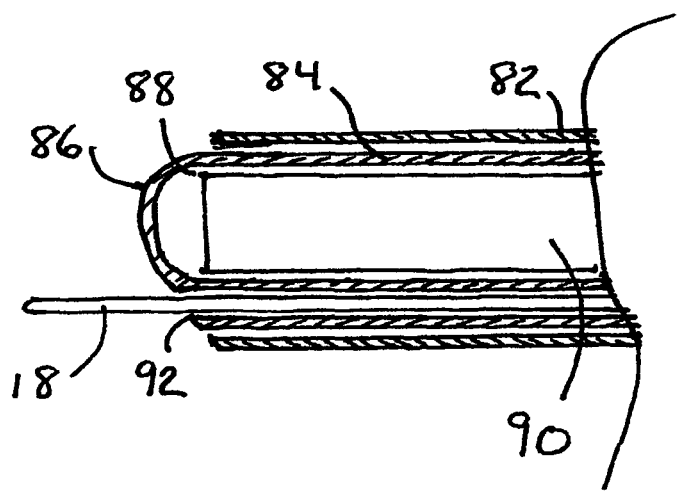
FIG. 6B is a partial cross-section view of a second optical dilator, with a stylet extending through the dilator and an endoscope disposed in the optical dilator.

FIGS. 6A and 6B illustrate an alternative dilating obturator and cannula assembly which may be used with the foregoing embodiments. More specifically, FIGS. 6A and 6B illustrate an optical dilating obturator which permits visualization as the optical dilating obturator and cannula assembly is inserted into the brain.

Referring now to FIG. 6A the optical dilating obturator and cannula assembly is configured to include a cannula 82 and a dilating obturator 84 having a transparent optical window 86 at the distal end of the obturator. Preferably, the transparent optical window is rounded, such as the semi-spherical window shown in FIG. 6A. As shown, a longitudinal channel 88 configured and dimensioned to receive an endoscope is provided in the obturator. An endoscope 90 is shown inserted into the endoscope channel in the dilating obturator. In use, the optical dilating obturator and cannula assembly may be used as in the embodiment of FIGS. 4 and 5 to visualize the brain tissue as the obturator and cannula assembly is inserted into the brain. Thus, the image acquired by the endoscope through the distal optical window may be observed as the obturator and cannula is inserted into the brain tissue. The image may be projected onto a monitor or screen for display for visualization as the obturator is inserted. If the optical dilating obturator and cannula assembly is used together with an image guidance system, the position of the instrumentation may be displayed in one image while the optical view through the endoscope is display in another.

FIG. 6B illustrates an optical dilating obturator and cannula assembly similar to that of FIG. 6A using like reference numerals for corresponding structures, but configured to accommodate stylet shaft 18 of the embodiment shown in FIGS. 1-3. As shown, optical dilating obturator 84 additionally includes a longitudinal stylet or probe channel 92 configured and dimensioned to receive the stylet or probe shaft 18. As in the embodiment of FIGS. 1-3, the stylet or probe is inserted through stylet or probe channel 92 until the stylet or probe 18 extends distally from the optical dilating obturator. With the optical dilating obturator and cannula assembly withdrawn proximally up the stylet shaft, the stylet or probe is inserted, preferable under image guidance, to a point adjacent to the target tissue. The optical dilating obturator and cannula are then moved distally to dilate and spread the brain tissue over the cannula. As the optical dilating obturator and cannula are advanced, the brain tissue being dilated may be visually observed through the endoscope, preferably by displaying the image on a monitor or screen.

After the optical dilating obturator and cannula have been inserted to dilate the brain tissue, the optical dilating obturator and stylet (if used) are removed, leaving the cannula in place to permit the surgeon to perform surgery through the cannula.

FIGS. 7-11 illustrate the use of the access device 10 of the first embodiment during minimally invasive brain surgery, as will now be described.

In FIG. 7, a partial cross-section view of the access device 10 with probe or stylet 16 inserted through an opening 100 formed in a patient s skull 102 through brain tissue until tip 24 of stylet 16 is adjacent target tissue 104. Opening 100 is made in a traditional manner, by incising the prepared and marked scalp, dissecting the scalp away from the underlying bony skull 102, retracting the scalp away from the area where hole 100 is to be formed, and then forming hole 100 using a drill, saw or similar apparatus in a known manner. After an opening has been formed in the skull, the dura overlying and protecting the brain is carefully incised and retracted to provide access to the brain. Stylet 16 is approximately 12 cm to 15 cm in length and approximately 3 mm in diameter and may be atraumatically urged through brain tissue until the target tissue is reached. Because stylet handle 20 is associated with imaging targets 22 the position of the stylet may be confirmed one or more times during insertion against pre-operative surgical planning images using an image guidance system. As shown in FIG. 8, once stylet 16 is placed, the dilating obturator with cannula is advanced carefully along the stylet so that the blunt rounded tip 30 atraumatically dilates the brain tissue. In FIG. 8, the dilating obturator is shown partially inserted into the brain, with blunt rounded tip 30 spreading the brain tissue as the obturator is advanced.

In FIG. 9, the access device is shown inserted into brain tissue until the tip of the dilating obturator is adjacent the target tissue. As shown, the brain tissue has been spread apart and surrounds cannula 12. With the access device fully inserted, the stylet and obturator are removed, leaving the open cannula 12 to provide surgical access to the target tissue, as illustrated in FIG. 10. The brain tends to occupy the space available within the skull and, as shown in FIG. 10, after the obturator is removed the target tissue will have a tendency to approach the open end of the cannula. If this does not naturally occur it may be desirable to separately advance the cannula forward either before or after removing the dilator so that the end of the cannula is located directly next to the target tissue.

Figure 11:
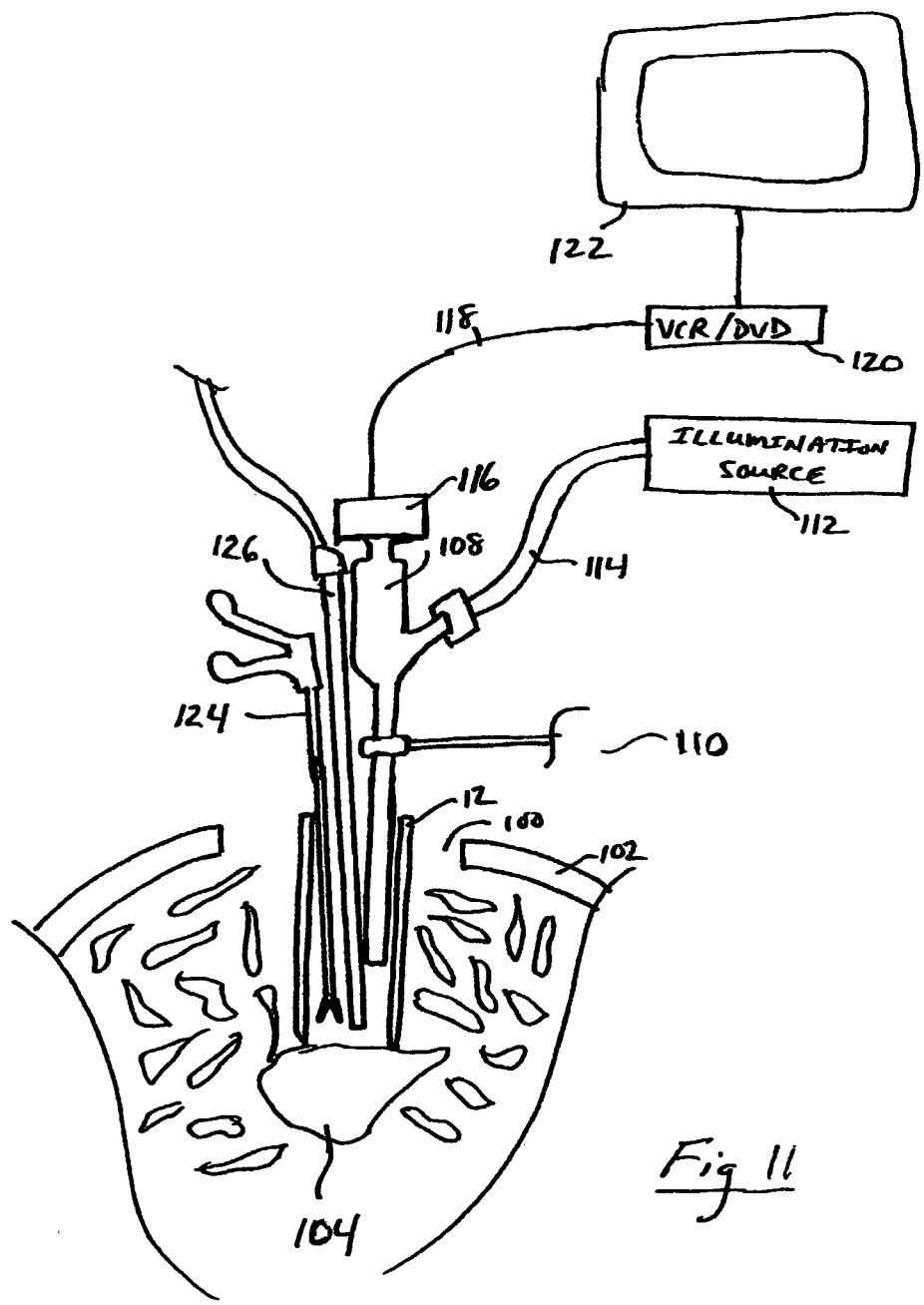
FIG. 11 is an illustration of an endoscope mounted partially within the cannula and a scissors and suction device inserted to debulk and remove target tissue.

After the access cannula is placed as shown in FIG. 10, surgery may be performed upon the target tissue through the cannula. In this regard, it is contemplated that cannula lengths of up to about 6 cm may be necessary or desirable, although a cannula length of about 4 cm should be sufficient to reach most areas of the brain where surgery is to be performed using the access device and methods described herein. It is also contemplated that the cannula may have an inner diameter of approximately 10 mm to 20 mm, and more preferably about 10 mm to 15 mm to allow multiple instruments, such as graspers, dissectors, scissors, and suction instruments to be inserted through the cannula to perform surgery. The cannula wall thickness may be on the order of from about 1 mm to about 3 mm. In the event removal of tissue is desired, a debulking suction irrigation device such as a CUSA device (Valleylab, Inc., Boulder Colo.) may be used. See, for example, Rose U.S. Pat. No. 6,083,191; Stoddard U.S. Pat. Nos. 6,214,017, 6,256,859, and 6,654,999; and Cimino U.S. Pat. No. 6,602,227. Alternatively, a scissor and separate suction tube may be used. In a preferred method of performing surgery illustrated in FIG. 11, an endoscope of approximately 4 mm diameter is partially inserted and held to one side of the cannula, and the image of the end of the cannula and the target tissue is projected onto a monitor for viewing by the operating surgeon, assistants and others. Advantageously, a recording of the surgery also may be made. In FIG. 11, the endoscope 108 is illustrated inserted into the cannula 12 and held in place by the arm 110 of a scope holding device, thereby eliminating the need for the surgeon or assistant to hold the scope. Endoscope 108 is attached to a source of illumination 112 by a light cable 114. While the endoscope can be used under direct vision utilizing the endoscope eyepiece, it is preferred to attach a camera 116 to the endoscope which in turn is attached via a cable 118 to a video device 120 such as a VCR or DVD with an accompanying monitor display 122. Recent advances in operating room display equipment permit large monitoring devices, such as flat panel displays to be used. The latter display is particularly useful for teaching or lecturing purposes, as it allows multiple persons to observe the surgical technique. Without such a display, it would be impractical to have numerous persons in the operating field attempting to observe the surgery. Live telesurgery also is contemplated. Also shown in FIG. 11 is a scissor 124 and suction tube 126 being used to debulk and remove target tissue 104. Preferably, at all times during insertion of the access device into the brain and during surgery through the cannula, the patient's brain function and condition is monitored so that the surgeon may be alerted in the event the patient becomes distressed or otherwise is adversely affected by the surgeon's actions. In the event signs of stress or adverse effects are noted, the surgeon may decide to continue the surgery, wait to see if the patient stabilizes, or terminate the procedure. Because of the sensitive nature of brain tissue and associated nerves and blood vessels, it is not uncommon for a surgeon to terminate a procedure before removing all target tissue in order to avoid the risk of serious adverse effects upon the patient.

Figure 12:
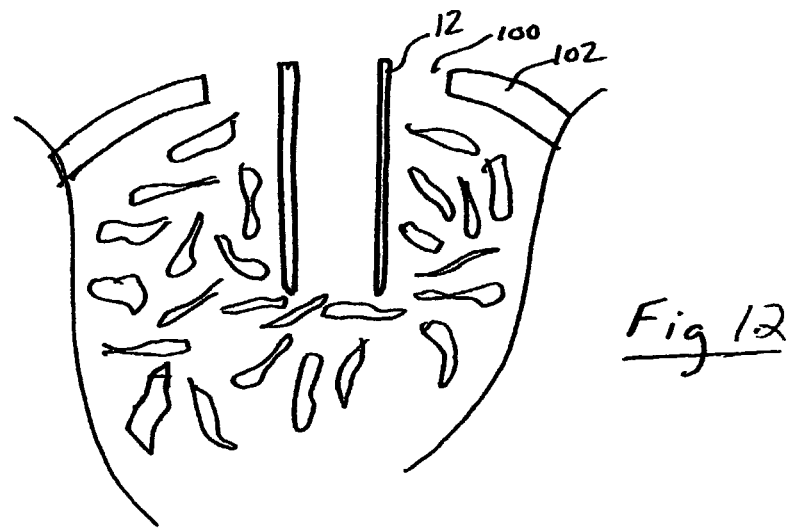
FIG. 12 is an illustration of a cannula in place after target tissue has been removed.
Figure 13:
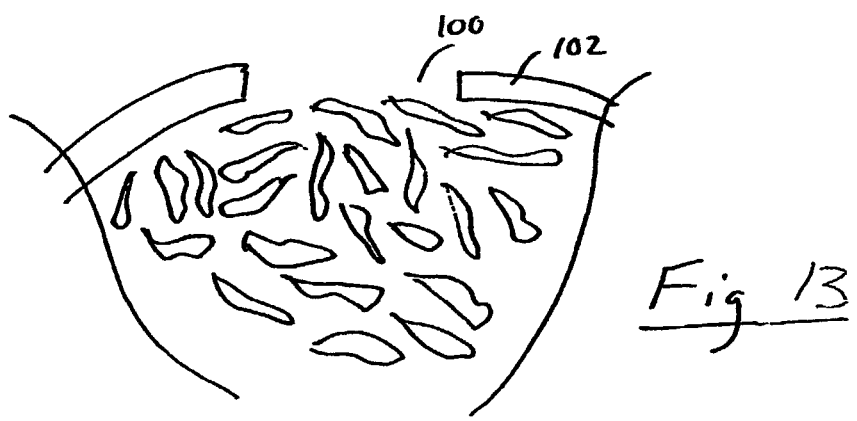
FIG. 13 is an illustration showing brain tissue having resumed its position occupying the space previously occupied by the cannula during surgery.

After surgery on the target tissue is complete, the instruments are removed from the cannula. As the target tissue is removed, the brain tissue fills the void formed by removing the target tissue so that healthy brain tissue underlying the now removed target tissue is adjacent the end of the cannula, as shown in FIG. 12. The cannula is then gently removed and the brain tissue naturally fills the space formerly occupied by the cannula, as shown in FIG. 13. This can take several minutes, but is relatively atraumatic. The dura, skull and scalp are closed in a known manner.

It is contemplated that the cannula may be from about 2 cm to about 6 cm in length, although different lengths may be desirable for particular situations. The cannula also preferably is clear, and is made to have a smooth outer surface to minimize trauma to the brain tissue. An important function of the cannula is to maintain the brain tissue in a separated condition to provide access and room to perform surgery. Just as important, however, is the function of the cannula to protect surrounding brain tissue from trauma due to contact with instruments during surgery. Thus, the cannula performs the dual functions of maintaining working space created during insertion of the obturator and cannula assembly and protecting surrounding brain tissue from trauma that might otherwise be caused during surgery by contact with surgical instruments. Alternate cross-sectional shapes for the cannula and obturator also are contemplated, such as square, oval, or elliptical. Of course, the dilating tip configuration may need to be altered in order to provide atraumatic dilation of the brain tissue if such alternate cross-sections are used. The circular cross-section and rounded tip of the dilating obturator illustrated in the accompanying drawings has been found to be satisfactory, and permits gentle back and forth rotation to be used during insertion to urge the blunt dissecting tip through the brain tissue.

In all of the foregoing embodiments, it is also contemplated that the proximal end of the cannula may include an annular flange or collar, as shown in FIG. 21, to facilitate handling and to prevent the cannula from advancing into the brain during surgery.

In accordance with the above description, the dilating obturator and cannula may be placed using a guide stylet which has previously been placed into the brain under image guidance. Alternative techniques for placing the stylet are contemplated. For example, rather than using image guidance, it is contemplated that the stylet may be placed using a stereotactic headframe, such as a Leksell frame (Elekta, of Sweden) or a GTC frame (Radionics, Burlington, Mass.). In a further alternative using such a headframe, the dilating obturator and cannula may be placed using such a headframe and eliminating the need for the stylet. Such stereotactic headframes and associated methods of approaching target tissue within the brain along a predetermined trajectory are shown and described in Cosman U.S. Pat. No. 6,331,180.

In the further alternative embodiment shown in FIG. 4, the dilating obturator equipped with image guidance means mounted directly to the obturator may be inserted under guidance without the use the stylet of the first embodiment. In using the embodiment of FIG. 4, the scalp and skull are opened in a traditional manner. Once access to the brain is established by opening and retracting the dura, dilating obturator 56 with cannula 52 mounted onto shaft 60 is urged through the brain tissue so that the rounded semi-spherical tip of the obturator atraumatically spreads the brain tissue until the target tissue is reached. As the dilating obturator is advanced, the position of the obturator may be checked using the image guidance system. Preferably, the obturator is pre-calibrated to the image guidance system. See, for example, Costales U.S. Pat. No. 5,921,992. In this regard, it is also contemplated that the image guidance means could be mounted to the cannula, but such an approach is less preferred because the image guidance means would remain attached to the cannula during surgery or the image guidance means would need to be removed from the cannula prior to surgery, adding another step to be performed. Attaching the image guidance means to the obturator accomplishes the objective of guiding placement of the cannula while also conveniently removing the image guidance means from the surgical field with the obturator after the cannula is placed so that the image guidance means does not obstruct the operative field.

Current image guidance systems superimpose an image of the instrument upon a pre-operative image of the patient s skull. As imaging techniques and equipment improve, it is contemplated that real time imaging will be available. Such real-time imaging techniques will be particularly useful with the techniques of the present method, as it will be possible to observe the position of the dilating obturator in relation to the real-time image of the brain structures rather than that by comparison to pre-operative images. The infrared image guidance reflectors shown in the first and second embodiments are used in connection with known optical image guidance systems. Such optical image guidance systems require a direct line of site between the image guidance balls and the camera of the image guidance system. While such optical image guidance may be used in the surgical methods described herein, it is contemplated that magnetic image guidance also may be well suited for use in the present method. As the name implies, a magnetic image guidance system uses magnetic forces to detect the position and orientation of the instrument. Because no direct line of site is require, the magnetic position sensors may be detected even while positioned within the skull. It is therefore contemplated that one or more magnetic position sensors may be positioned at or near the tip of the dilating obturator so that the position of the tip may be more directly detected and displayed. One electromagnetic guidance system is available from the Visualization Technologies division of GE Medical Systems. Compare Ferre U.S. Pat. Nos. 5,676,673, 5,800,352, 5,803,089, 5,829,444, 5,873,822, 5,967,980, 6,175,756, 6,341,231, and 6,445,944.

While the preferred method utilizes image guidance to guide insertion of the dilating obturator and, hence, placement of the cannula, it is understood that it is possible to insert the dilating obturator without image guidance. Thus, the third embodiment of FIG. 5 consists only of a dilating obturator and cannula assembly without any associated image guidance apparatus. In use, the dilating obturator 76 with cannula 72 over the shaft 80 is inserted under direct visualization through brain tissue until the blunt rounded, semi-spherical obturator tip is adjacent to the target tissue. An experienced surgeon also may find it useful to inspect pre-operative images displayed on the monitor simultaneous with insertion of the obturator so that the surgeon may compare the pre-operative image to what is visible during insertion of the obturator under direct visualization. After the obturator and cannula of FIG. 5 has been inserted, the obturator is removed as in prior embodiments to leave the cannula in place as shown in FIG. 10.

Thereafter, surgery is preformed through the cannula. After surgery, the cannula is removed and the dura, skull and scalp are closed in a traditional manner.

Figure 14:
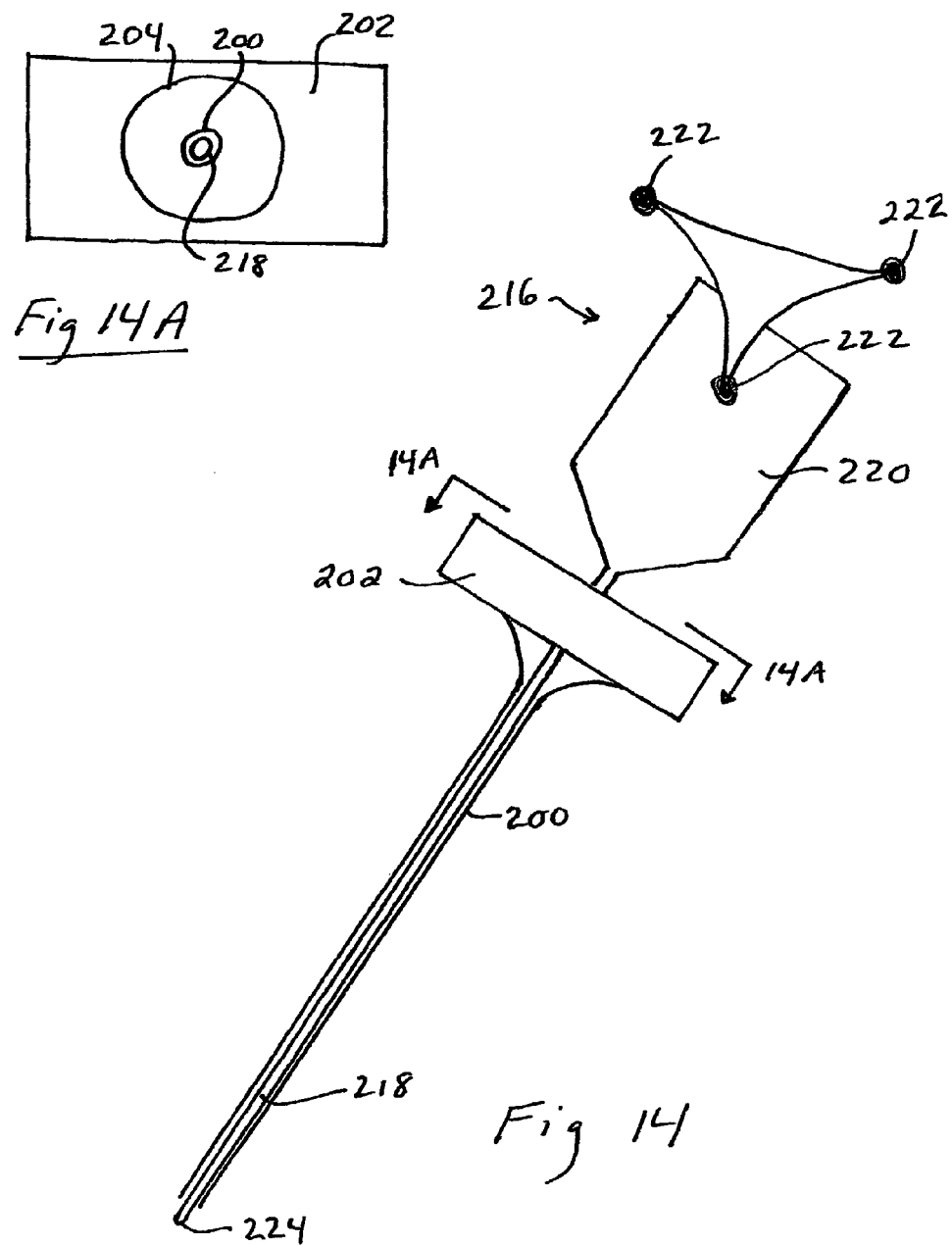
FIG. 14 is a perspective view of a stylet with an expandable sleeve.
Figure 15:
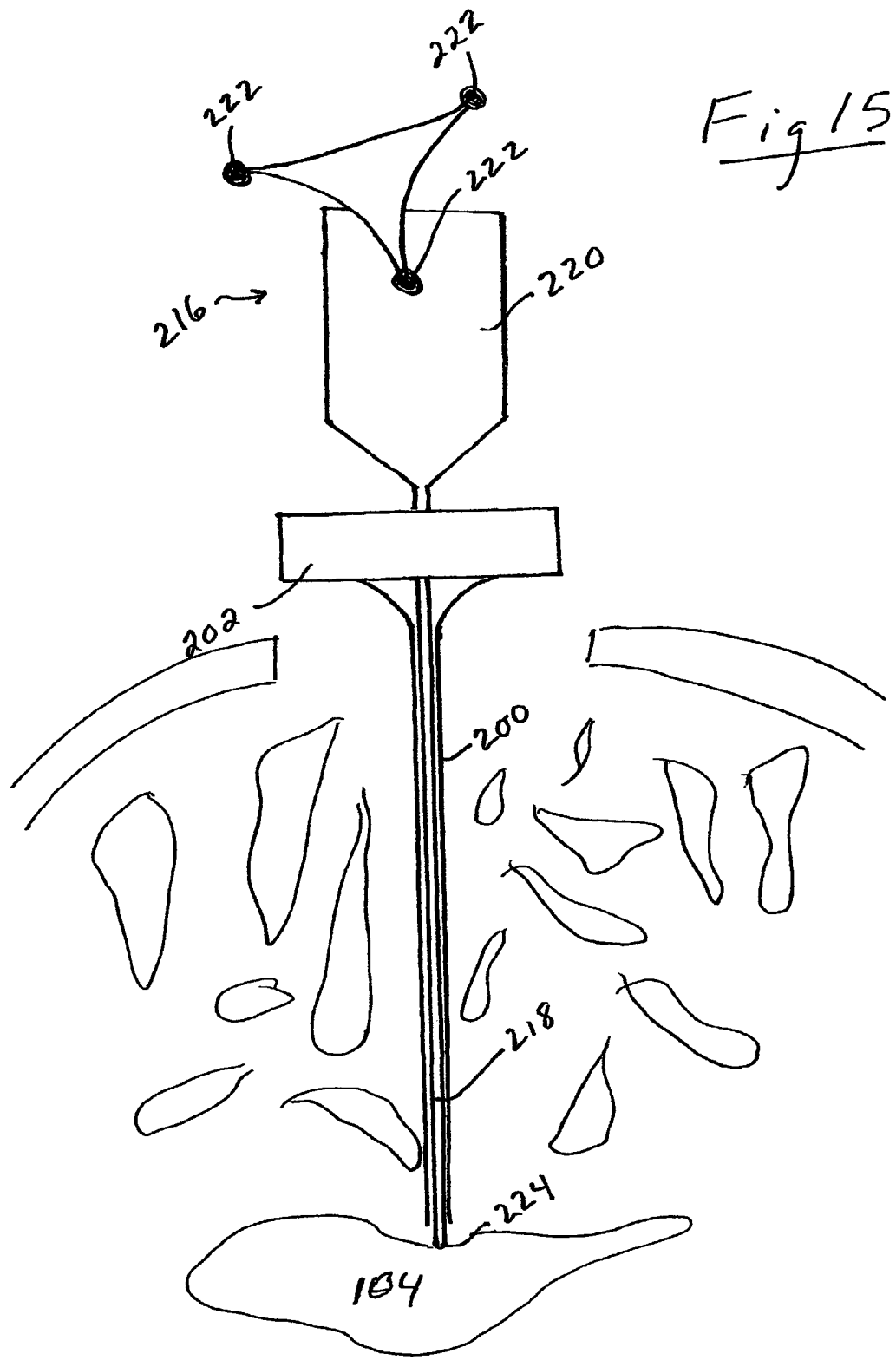
FIG. 15 is an illustration of the embodiment of FIG. 14 inserted into brain tissue.
Figure 16:
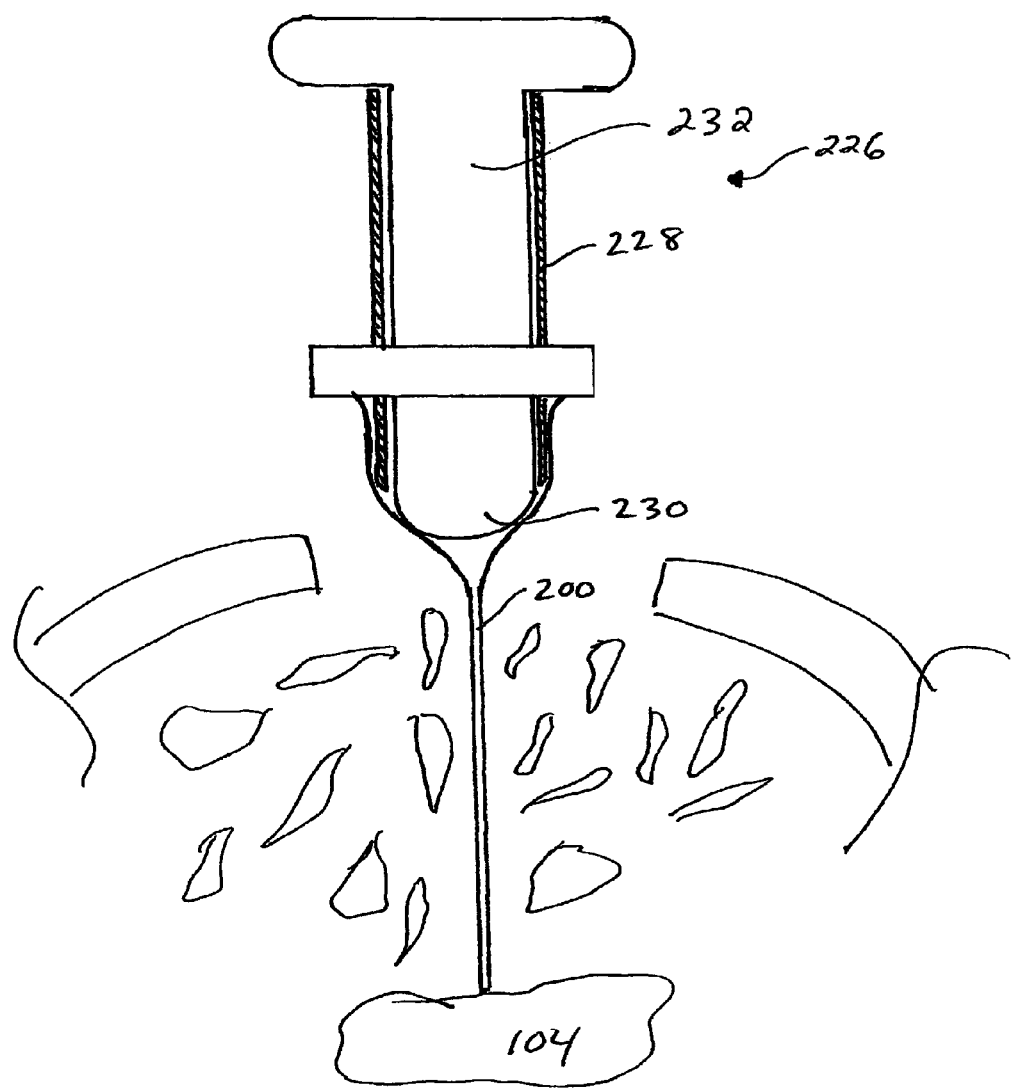
FIG. 16 is an illustration of the embodiment of FIGS. 14 and 15, with the stylet removed and a dilating obturator and cannula assembly inserted into and expanding the expandable cannula.

Referring now to FIGS. 14-16, an alternative structure for creating surgical access is shown. In this embodiment, an expandable sleeve 200 is mounted to a sleeve hub 202, such as by capturing the end of the sleeve between two parts of the hub which are snapped or welded together during assembly. As shown in FIG. 14A, which is a cross-section view taken along lines 14A-14A of FIG. 14, hub 202 has a bore 204 configured and dimensioned to allow a dilating obturator and cannula assembly to be inserted through the hub into the expandable sleeve 200. A stylet or probe 216 having a shaft 218 is inserted through the hub bore 204 and through the sleeve 200 with sleeve 200 in an unexpanded state. Stylet 216 preferably includes a handle 220 and image guidance reflectors 222 similar to the embodiment shown in FIGS. 1-3. By way of example only, sleeve 200 may have an outer diameter on the order of 3 mm to 4 mm with the stylet shaft 218 inserted therethrough.

Referring to FIG. 15, in use stylet shaft 218 with sleeve 200 mounted thereon is inserted through bore hole 100 in the skull 102 into the brain until tip 224 of shaft 218 is adjacent target tissue 104, preferably using image guidance.

Figure 17:
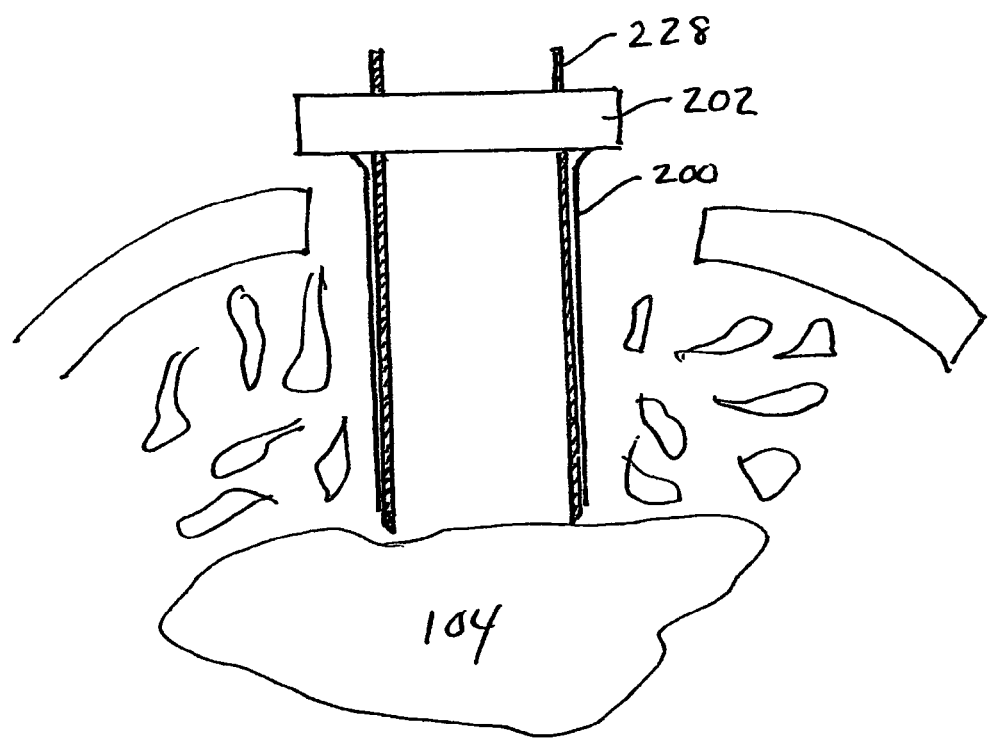
FIG. 17 is an illustration of the embodiment of FIG. 16 with the dilating obturator removed to provide a cannula in the expandable sleeve to provide access to the target tissue.

As shown in FIG. 16, after the expandable sleeve is inserted adjacent target tissue 104, stylet 216 is withdrawn, leaving expandable sleeve 200 in place. Thereafter, dilating obturator and cannula assembly 226 is inserted through bore 204 in hub 202, such that the blunt dilating tip 230 of the dilating obturator, which may be conical, rounded, semi-spherical (as shown) or other suitable atraumatic shape, spreads the expandable sleeve 200 to dilate the brain tissue and receive cannula 228. Once the obturator and cannula assembly 230 has been inserted, the dilating obturator 232 is removed, leaving cannula 228 surrounded by expandable sleeve 200 in place to provide access to target tissue 104 for surgery to be performed as previously described, as shown in FIG. 17.

Figure 18:
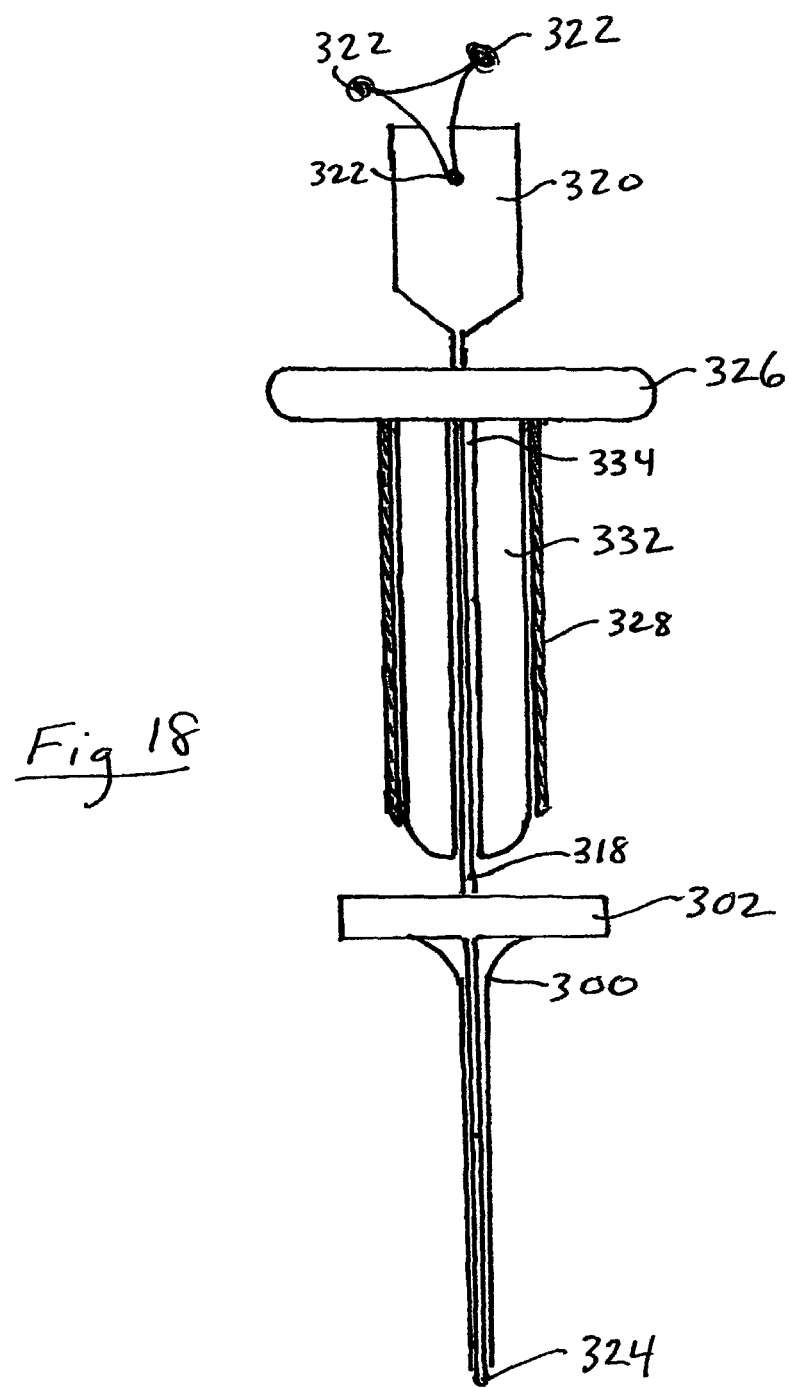
FIG. 18 is a cross-section view of an expandable sleeve device with the stylet disposed within the expandable sleeve and a dilating obturator and cannula assembly mounted over the stylet shaft proximal to the expandable sleeve.

In an alternative configuration shown in FIG. 18, dilating obturator 332 is provided with a longitudinal channel 334 configured and dimensioned to receive stylet or probe shaft 318. In this embodiment, the dilating obturator and cannula assembly is pre-mounted to the stylet or probe shaft 318. Shaft 318 is of sufficient length to accommodate both the expandable sleeve assembly and the dilating obturator/cannula assembly in stacked end to end relation. In use, the stylet shaft 318 with the surrounding sleeve is inserted into the brain under image guidance (reflectors 322 allow orientation of the entire assembly under image guidance). Once the stylet and sleeve are placed, the dilating obturator and cannula assembly may be slid distally over the stylet shaft 318 so that sleeve 200 expands over the dilating tip and cannula, gently spreading the brain tissue sufficiently to receive cannula 328. This may be accomplished by holding hub 302 in one hand and obturator handle 326 in the other, and moving the obturator distally while maintaining the position of the stylet and expandable sleeve. An advantage of this configuration is that the position of the stylet tip 324 relative to target tissue 104 may be confirmed under image guidance at one or more intervals as the dilating obturator and cannula assembly is inserted into the expandable sleeve, thereby assuring proper cannula placement. Alternative configurations are contemplated. For example, image guidance reflectors may be mounted to the dilator to be used with the embodiment shown in FIG. 16 either in addition to or in place of image guidance reflectors on the stylet or probe assembly. It is also contemplated that the optical dilating obturator of FIGS. 6A-6B may be used with the expandable sleeve embodiments of FIGS. 14-18.

Figure 19A:
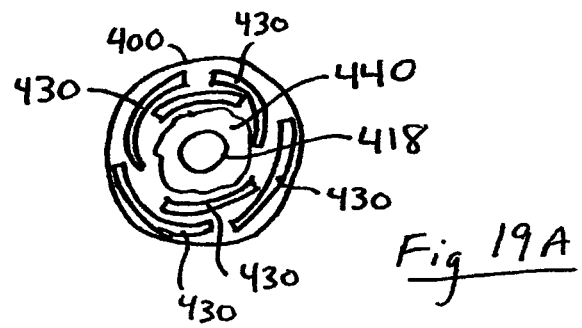
FIGS. 19A and 19B are cross-section views of an expandable sleeve with a balloon-actuated radially expandable cannula.
Figure 19B:
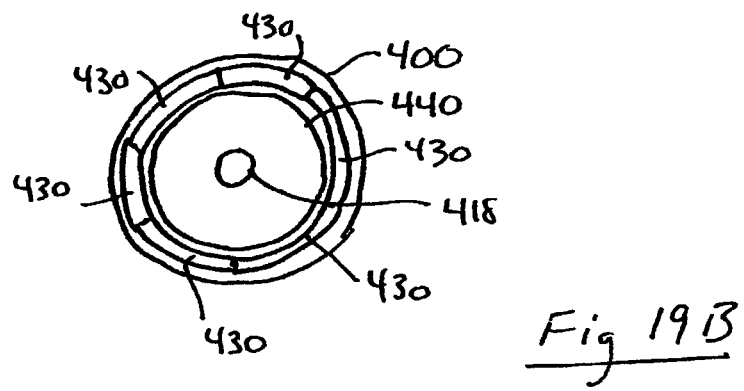

In yet a further embodiment of the expandable sleeve approach shown in FIGS. 19A and 19B, the cannula may be inserted in collapsed segments contained within the expandable sleeve and inserted together with the stylet and expandable sleeve. A radial force is applied to urge the cannula wall segments radially outward, thereby expanding the expandable sleeve and establishing the full cannula opening. The cannula wall segments lock in place in a manner similar to a Roman arch to support the expanded sleeve and create a working space. The radial force to expand the cannula segments may be created by a balloon, which desirably may be collapsed to a very low profile and yet may create the desired radial force to expand the sleeve, dilate the brain tissue and lock the cannula wall segments in place. Alternatively, coil or spring structures may be used to create the desired radial force to expand the sleeve and cannula.

Referring to FIGS. 19A and 19B, an example of a balloon expanded cannula/sleeve assembly is shown in cross section at a point along the shaft of the expandable sleeve device. As shown in FIG. 19A, stylet shaft 418 is at the center of the structure, surrounded in radially outward order by a collapsed balloon 440, overlapping cannula wall sections 430 and expandable sleeve 400. All components extend the length of the expandable sleeve. The tip of stylet shaft 418 is inserted into brain tissue until the stylet tip and, hence, the distal end of the expandable sleeve is placed adjacent the target tissue, preferably using image guidance. Balloon 440 is expanded, such as by being filled under pressure with saline. The pressure created in the balloon forces the cannula wall segments 430 radially outward until the wall segments lock in place. See FIG. 19B. As the cannula wall segments are moved radially outward and lock into place, expandable sleeve 400 is in turn expanded outward to dilate surrounding brain tissue. Once the cannula walls are locked out, the balloon may be deflated and the stylet and balloon removed, leaving an open cannula to access and perform surgery on target brain tissue.

The radial expanding sleeve may provide advantages in performing brain surgery. First, because longitudinal force is not utilized to expand the sleeve, there is less likelihood that the expandable sleeve will inadvertently be advanced further into the brain during expansion. Furthermore, because radial force is generated along the length of the stylet and cannula, no blunt dilating tip extends beyond the cannula after dilating brain tissue, as may occur with the use of a longitudinal advancement of a dilating obturator.

Figure 20A:
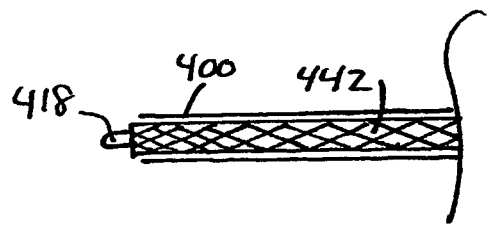
FIGS. 20A and 20B are partial cross section views illustrating an alternative structure for radially expanding an expandable sleeve.
Figure 20B:
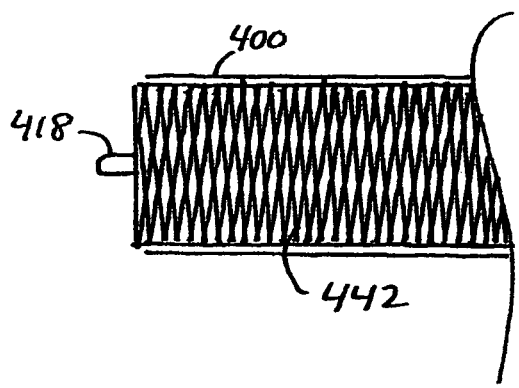

Referring now to FIGS. 20A and 20B, an alternative structure for radially expanding sleeve 400 is shown in which shortening the length of an expanding structure 442 radially expands sleeve 400. As shown in FIG. 20A, in a first position expanding structure 42 has a first braid angle and a relatively small radial width. As shown in FIG. 20B, with the distal end of expanding structure 442 constrained against longitudinal movement, such by tethering the end of the braided structure, the proximal end of the braid is urged distally so that the braid shortens. The distal end of the braid could be tethered, for example, by a plurality of longitudinally extending wires or filaments circumferentially disposed around the braid running the length of the braid to the distal end thereof. As the braid is shortened, the braid angle decreases and the diameter of the braid increases, thereby expanding the sleeve to create the desired diameter of sleeve for working access to the target tissue. Because the force required to dilate brain tissue is relatively low, shortening the braid may develop sufficient force to radially expand the sleeve, and consequently the surrounding brain tissue. It is also contemplated that the approach of shortening a braid to create radial force could be used to open cannula segments 430 (see FIGS. 19A and 19B) to their open, locked position.

In all of the foregoing embodiments the surgeon is provided an open cannula to access target tissue within the brain. Advantageously, the open cannula is placed atraumatically which may allow surgery to be performed deeper in the brain or in areas of the brain previously believed to be inaccessible without high risk of advance consequences for the patient.

Numerous modifications and additions to the embodiments shown or described herein will become apparent to those skilled in the art based on this disclosure, and the disclosure is not intended to be limiting with respect to such additions or modifications. By way of example, although not shown it is contemplated that the proximal end of the cannula in all embodiments may be mounted to a housing or handle to facilitate control and movement of the cannula. By way of further example, such a cannula housing could couple to the expandable cannula housing (see FIGS. 14-18) to positively position the cannula with respect to the expandable sleeve housing and, hence, the expandable sleeve.

The techniques described herein are particularly useful to access tumors, cysts or other conditions which might otherwise be considered inoperable or might require much more invasive transcranial surgery to remove a larger portion of the skull and retract a substantial amount of brain tissue. The techniques described herein using dilating obturator and cannula permit brain surgery to be performed in a less invasive manner through an opening in the skull that is substantially smaller then otherwise possible, on the order of a 2 cm to 4 cm in diameter rather than a much larger opening for more traditional surgical techniques.

What is claimed is:

1. A method of performing brain surgery comprising:
identifying target tissue located within a brain;
accessing the brain through an opening formed through a skull;
advancing a blunt dilating obturator having a shaft portion and an optically transparent tip at a distal end thereof into the brain over a stylet with a cannula mounted over the shaft portion to atraumatically dilate brain tissue while visualizing brain tissue through the optically transparent tip until the blunt dilating obturator is positioned adjacent the target tissue, wherein the stylet is placed into brain tissue under image guidance; and
removing the blunt dilating obturator leaving the cannula in place to provide access to the target tissue.

2. The method of claim 1 wherein advancing the blunt dilating obturator and the cannula further includes atraumatically spreading brain tissue until the brain tissue surrounds the cannula.

3. The method of claim 1 further including performing surgery on the target tissue through the cannula.

4. The method of claim 3 further including inserting an endoscope into the cannula and performing surgery on the target tissue while visualizing the target tissue on a monitor.

5. The method of claim 3 further including removing the cannula from the brain after performing surgery.

6. The method of claim 3 further including monitoring brain function during surgery.

7. The method of claim 1 further including breaking up and removing the target tissue through the cannula.

8. The method of claim 1 further including providing a transparent cannula and viewing brain tissue through a wall of the cannula.

9. The method of claim 1 wherein advancing the blunt dilating obturator until the blunt dilating obturator is positioned adjacent target tissue further includes advancing the blunt dilating obturator under image guidance.

10. The method of claim 1 wherein advancing the blunt obturator and the cannula further includes providing the cannula with a cannula diameter of from about 10 mm to 15 mm and a cannula length of from about 2 cm to 6 cm.

* * * * *